US005951993A

United States Patent [19]
Scholz et al.

[11] Patent Number: 5,951,993
[45] Date of Patent: Sep. 14, 1999

[54] STABLE HYDROALCOHOLIC COMPOSITIONS

[75] Inventors: Matthew T. Scholz, Woodbury, Minn.; Robert A. Asmus, Hudson, Wis.; Jill R. Charpentier, Minnetonka, Minn.

[73] Assignee: Minnesota Mining and Manufacturing Company, St. Paul, Minn.

[21] Appl. No.: 08/781,090

[22] Filed: Jan. 9, 1997

Related U.S. Application Data

[63] Continuation-in-part of application No. 08/493,714, Jun. 22, 1995, abandoned.

[51] Int. Cl.$^6$ .................................................. A01N 25/30
[52] U.S. Cl. .................... 424/405; 424/667; 510/132; 510/157; 514/635; 514/944; 514/975
[58] Field of Search ..................... 424/405, 667; 510/130, 131, 132, 157, 158, 382, 383, 384, 385, 403, 404; 514/635, 873, 944, 975

[56] References Cited

U.S. PATENT DOCUMENTS

| | | | |
|---|---|---|---|
| 2,054,989 | 9/1936 | Moore | 167/58 |
| 2,153,143 | 4/1939 | Figg, Jr. et al. | 87/5 |
| 2,678,902 | 5/1954 | Mehaffey | 167/91 |
| 3,131,152 | 4/1964 | Klausner | 252/305 |
| 3,131,153 | 4/1964 | Klausner | 252/305 |
| 3,395,214 | 7/1968 | Mummert | 424/47 |
| 3,415,939 | 12/1968 | Minton | 424/357 |
| 3,840,465 | 10/1974 | Knowles et al. | 252/90 |
| 4,006,218 | 2/1977 | Sipos | 424/54 |
| 4,199,564 | 4/1980 | Silver et al. | 421/80 |
| 4,202,881 | 5/1980 | Gross et al. | 424/70 |
| 4,254,104 | 3/1981 | Suzuki | 424/170 |
| 4,464,293 | 8/1984 | Dobrin | 252/547 |
| 4,478,853 | 10/1984 | Chaussee | 424/358 |
| 4,501,834 | 2/1985 | Su | 524/28 |
| 4,511,486 | 4/1985 | Shah | 252/90 |
| 4,542,012 | 9/1985 | Dell | 424/28 |
| 4,559,226 | 12/1985 | Fogel et al. | 424/66 |
| 4,584,192 | 4/1986 | Dell et al. | 424/81 |
| 4,671,957 | 6/1987 | Holtshousen | 424/80 |
| 4,695,453 | 9/1987 | Tuominen et al. | 424/81 |
| 4,719,239 | 1/1988 | Muller et al. | 514/23 |
| 4,752,612 | 6/1988 | Saito et al. | 514/420 |
| 4,806,262 | 2/1989 | Snyder | 252/90 |
| 4,831,023 | 5/1989 | Garlen et al. | 514/169 |

(List continued on next page.)

FOREIGN PATENT DOCUMENTS

| | | |
|---|---|---|
| B-72440/87 | 11/1987 | Australia . |
| 0 014 502 A1 | 8/1980 | European Pat. Off. . |
| 0 223 681 A1 | 5/1987 | European Pat. Off. . |
| 0 260 641 A2 | 3/1988 | European Pat. Off. . |
| 0 289 160 A1 | 4/1988 | European Pat. Off. . |
| 0 381 618 A1 | 8/1990 | European Pat. Off. . |
| 0 451 949 A1 | 10/1991 | European Pat. Off. . |
| 0 522 624 A1 | 1/1993 | European Pat. Off. . |
| 0 689 767 A2 | 1/1996 | European Pat. Off. . |
| 0 745 389 A1 | 12/1996 | European Pat. Off. . |
| 788 811 | 10/1935 | France . |
| 2 406 438 | 5/1979 | France . |
| 34 16 777 A1 | 11/1985 | Germany . |
| 36 32 030 A1 | 3/1988 | Germany . |
| 80 92 078 | 4/1996 | Japan . |
| 1 527 781 | 10/1978 | United Kingdom . |
| WO 93/07903 | 4/1993 | WIPO . |
| WO 94/13354 | 6/1994 | WIPO . |
| WO 95/03772 | 2/1995 | WIPO . |
| WO 97/00667 | 1/1997 | WIPO . |

OTHER PUBLICATIONS

Yamashita et al. Surfactants, Polymeric (Overview) in: Polymeric Materials Encyclopedia, Salamone, J.C. Editor. CRC Press (1996) vol. 10. pp. 8195–8201.

BIOSIS Abstract 80:188 400, Abstract of *Zentralbl Bakteriol Parasitenkd Infektionskr Hyg Erst Abt Orig Reihe B Hyg Krankaenhaushyg Betriebshyg Praev Med*, 168, pp. 5–6 (1979).

BIOSIS Abstract 86:434 601, Abstract of *Hyg. Med.*, 11, pp. 238–241 (1986).

Bulletin No. 51–0001–259, Specialty Chemicals of ICI America of Wilmington, DE.

J.L. Cohen et al., "Penetration of 5–Fluorouracil In Excised Skin", *The J. of Investigative Dermatology*, 62, pp. 507–509 (1974).

CTFA Cosmetic Ingredient Handbook, Published by The Cosmetic, Toiletry and Fragrance Association, Inc., pp. 37, 64–65, 78, 81 (1988).

G.M. Eccleston, "Application of Emulsion Stability Theories to Mobile and Semisolid O/W Emulsions", *Cosmetics & Toiletries*, 101, pp. 73–92 (1986).

G.M. Eccleston, "Influence of long chain alcoholics (or acids) and surfactants on the stabilities and consistencies of cosmetic lotions and creams", *Cosmetics and Toiletries*, 92, pp. 21–28 (1977).

E.D. Goodard et al., "Novel gelling structures based on polymer/surfactant systems", *J. Soc. Cosmet. Chem.*, 42, pp. 19–34 (1991).

P.B. Price, "Reevaluation Of Ethyl Alcohol As A Germicide", *Archives of Surgery*, pp. 492–502 (Undated).

R.B. Stoughton, "Vasoconstrictor Activity and Percutaneous Absorption of Glucocorticosteroids", *Arch. Derm.*, 99, pp. 753–756 (1969).

"Textbook of Polymer Science", F.W. Billmeyer, Ed.; Wiley–Interscience, NY; $2^{nd}$ Edition; pp. 84–85 (1971).

*Primary Examiner*—Robert H. Harrison
*Attorney, Agent, or Firm*—Robert W. Sprague; Jeffrey J. Hohenshell

[57] ABSTRACT

Disclosed is a composition including a lower alcohol and water in a weight ratio of about 35:65 to 100:0, between at least 0.5% and 8.0% by weight thickener system comprised of at least two emulsifiers, each emulsifier present in at least 0.05% by weight wherein the composition free of auxiliary thickeners has a viscosity of at least 4,000 centipoise at 23 degrees C. and wherein each emulsifier is comprised of at least one hydrophobic group and at least one hydrophilic group. The composition is useful as a presurgical scrub replacement, a lotion or other hand preparation.

80 Claims, No Drawings

U.S. PATENT DOCUMENTS

| | | | |
|---|---|---|---|
| 4,839,167 | 6/1989 | Yamamoto et al. | 424/71 |
| 4,883,660 | 11/1989 | Blackman et al. | 514/255 |
| 4,915,934 | 4/1990 | Tomlinson | 424/45 |
| 4,931,282 | 6/1990 | Asmus et al. | 424/448 |
| 4,956,170 | 9/1990 | Lee | 424/81 |
| 4,957,908 | 9/1990 | Nelson | 514/55 |
| 4,981,678 | 1/1991 | Tomlinson | 424/45 |
| 5,120,716 | 6/1992 | Miyazawa et al. | 514/23 |
| 5,128,123 | 7/1992 | Brewster et al. | 424/65 |
| 5,149,719 | 9/1992 | Ferber et al. | 514/772 |
| 5,164,107 | 11/1992 | Khan et al. | 252/106 |
| 5,167,950 | 12/1992 | Lins | 424/47 |
| 5,180,061 | 1/1993 | Khan et al. | 206/570 |
| 5,180,584 | 1/1993 | Sebag et al. | 424/401 |
| 5,223,261 | 6/1993 | Nelson et al. | 424/443 |
| 5,225,473 | 7/1993 | Duan | 524/388 |
| 5,232,691 | 8/1993 | Lemole | 424/78.02 |
| 5,298,182 | 3/1994 | Tsao et al. | 252/106 |
| 5,298,242 | 3/1994 | Vanlerberghe et al. | 424/78.36 |
| 5,334,388 | 8/1994 | Hoang et al. | 424/402 |
| 5,362,484 | 11/1994 | Wood et al. | 424/70 |
| 5,409,966 | 4/1995 | Duan et al. | 522/152 |
| 5,484,597 | 1/1996 | Slavtcheff et al. | 424/401 |
| 5,512,199 | 4/1996 | Khan et al. | 252/106 |
| 5,585,092 | 12/1996 | Trandai et al. | 424/65 |
| 5,626,853 | 5/1997 | Bara et al. | 424/401 |
| 5,629,006 | 5/1997 | Hoang et al. | 424/405 |

STABLE HYDROALCOHOLIC COMPOSITIONS

This application is a continuation-in-part of application Ser. No. 08/493,714, filed Jun. 22, 1995, abandoned, which is incorporated herein by reference.

FIELD OF THE INVENTION

The present invention relates to compositions useful as skin disinfectants, surgical hand preparations, patient skin preparations and antimicrobial hand lotions. More specifically the invention relates to stable hydroalcoholic compositions which are thickened using mixed emulsifier systems.

BACKGROUND OF THE INVENTION

Control of nosocomial infection and exposure to infectious disease is of paramount concern to doctors, nurses, and clinicians who work in hospitals and surgery centers. One of the most effective methods for controlling infection is regimented hand disinfection before and possibly after each patient contact and particularly before and after each surgical procedure. Hand disinfection is generally accomplished using antimicrobial soaps with water. These soaps are usually formulated to include either povidone-iodine (usually 7.5% by weight) or chlorhexidine gluconate (CHG) (usually 2 or 4% by weight) as the active antimicrobial agent. In addition, these formulated soaps may contain surfactants and possibly low levels of humectants such as glycerin.

Hand disinfection is also accomplished using presurgical scrub replacements. These are used instead of the soap and water scrub. Presurgical scrub replacements ideally achieve bacterial kill equal to or better than a traditional soap and water scrub and in a shorter period of time. Additionally, they maintain or improve the skin's natural barrier to microbial and chemical contamination while providing acceptable tactile properties. Examples of presurgical scrub replacements include hydroalcoholic gels which generally include high levels of either ethanol or isopropanol as the disinfecting agent and also include a thickener and optionally include a humectant (e.g. glycerin). To date, thickeners used in hydroalcoholic gels have been based on anionic polymers such as polyacrylic acid (sold under the tradename Carbopol by BF Goodrich Specialty Polymers and Chemicals Division of Cleveland, Ohio). U.S. Pat. No. 4,915,934 to Tomlinson discloses the use of CHG-containing antiseptic foams based on hydroalcoholic solvents, a fatty alcohol, and a surfactant. The surfactant is selected from the group of ethoxylated sorbitan alkylates, ethoxylated fatty alcohols, and ethoxylated nonyl phenols.

Formulating stable viscous hydroalcoholic emulsions is difficult for two reasons. First, addition of short chain alcohols (such as ethanol) to an aqueous system decreases the surface tension dramatically. For example, 40% by weight ethanol in water has a surface tension of approximately 31 dyne/cm compared to pure water which has a surface tension of about 72 dyne/cm at 20° C. A hydroalcoholic solution at 60% by weight ethanol has a dramatically decreased surface tension as compared to water. Such a composition has a surface tension of approximately 27 dyne/cm at 20° C. Second, many surfactants typically used in cosmetic emulsions become completely or partially soluble in hydroalcoholic systems.

In bulletin 51-0001-259 regarding skin care, Specialty Chemicals of ICI America of Wilmington, Del. stated that although ethanol can provide several benefits to skin care emulsions, formulators often avoid ethanol as it is difficult to prepare stable emulsions in its presence. In fact, the bulletin continued that ethanol is often used to break emulsions.

U.S. Pat. No. 4,956,170 to Lee discloses a hydroalcoholic skin moisturizing/conditioning antimicrobial gel. The gel comprises 60–75% ethanol and 0.4–2% of a polymeric thickening agent. The formulations also comprise polyethoxylated non-ionic surfactants/emulsifiers to stabilize the added emollient oils in addition to a fatty alcohol.

U.S. Pat. No. 5,167,950 to Lins discloses an antimicrobial aerosol mousse having a high alcohol content. The mousse comprises alcohol, water, a polymeric gelling agent and a surfactant system comprising a C16–C22 alcohol, aerosol propellant and a non-ionic polyethoxylated surfactant.

SUMMARY OF THE INVENTION

This invention provides compositions useful as products for skin disinfection such as presurgical hand preps, patient preps, and lotions. The preferred formulations of this invention, in general, have a very nice feel after both single and multiple applications. Additionally, preferred formulations maintain or improve the skin condition after multiple applications and no slimy or abnormal feeling is noticed during post application hand washing. When used as a presurgical scrub replacement, this invention achieves bacterial, fungal, and viral kill equal to or better than a traditional soap and water scrub in a shorter period of time while maintaining or improving the skin's natural barrier to microbial and chemical contaminants. The invention overcomes the shortcomings of past compositions by providing a viscous composition which includes a high concentration of a lower alcohol but does not require a polymeric thickener to make the composition viscous. Further, the composition has a cosmetically elegant feel and may be dispensed as a lotion or as a foam.

This invention provides a composition comprising a lower alcohol and water in a weight ratio of about 35:65 to 100:0, between at least 0.5% and 8.0% by weight thickener system comprised of at least two emulsifiers, each emulsifier present in at least 0.05% by weight wherein the emulsifiers are selected such that the composition free of auxiliary thickeners has a viscosity of at least 4,000 centipoise at 23 degrees C. and wherein each emulsifier is comprised of at least one hydrophobic group and at least one hydrophilic group, wherein: (i) the hydrophobic group is comprised of an alkyl group of at least 16 carbon atoms; an alkenyl group of at least 16 carbon atoms; or an aralkyl or an aralkenyl group of at least 20 carbon atoms; and (ii) the hydrophilic group of at least one emulsifier is comprised of an amide group having the structure —NHC(O)R''' or —C(O)NHR''' where R''' is hydrogen or an alkyl group of 1–10 carbon atoms optionally substituted in available positions by N, O, and S atoms; an ester group of short chain alcohols or acids (e.g., L=—C(O)OR' or —OC(O)R' where R' is C1–C4 branched or straight chain alkyl optionally substituted in available positions by hydroxyl groups); a polyglucoside group having 1–10 glucose units; a polyglycerol ester group having 1–15 glycerol units, a secondary amine group; a tertiary amine group; a quaternary amine group; an anionic group such as a sulfate, sulfonate, phosphate, phosphonate, or carboxylate group; or a zwitterionic group having the formula:

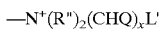

or

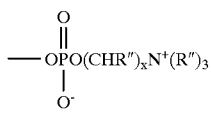

wherein each R" is independently hydrogen or an alkyl group (having 1–5 carbon atoms) or alkenyl group (having 2–4 carbon atoms), which alkyl or alkenyl groups are optionally substituted with nitrogen, oxygen, or sulfur atoms, including alkyl or alkenyl carboxyl groups; Q is hydrogen or hydroxyl; x is 1 to 4; and L' is $-CO_2^-$, $-OP(O)(O^-)(O^-M^+)$, $-(O)P(OR''')(O)(O^-M^+)$ (where R''' is hydrogen or an alkyl group of 1–10 carbon atoms optionally substituted in available positions by N, O, or S atoms), $-SO_2O^-$, or $-OSO_2O^-$, where $M^+$ is a positively charged counterion present in a molar ratio necessary to achieve a net neutral charge on the emulsifier and is selected from the group of hydrogen, sodium, potassium, lithium, ammonium, calcium, magnesium, or $N^+R''_4$; as well as combinations of these groups; and (iii) the hydrophilic group of at least one emulsifier is comprised of an alcohol group; an ethylene oxide/propylene oxide copolymer group having 2–150 moles of ethylene oxide plus propylene oxide per mole of hydrophobe ("R") and bonded to the hydrophobe through an ether or ester linkage, and optionally terminated by C1–C36 alkyl or C6 to C36 alkaryl ester; an ester or ether group of a polyhydric alcohol and their polyalkoxylated derivatives; an ester or ether of sorbitan or polyalkoxylated sorbitan group, as well as combinations of these groups. Thus, it will be understood by one of skill in the art that the emulsifiers can include combinations of all "L" hydrophilic groups described herein (e.g., ester groups and amide groups in one molecule).

This invention further provides a method of preparing a stable hydroalcoholic composition comprising the steps of preparing a thickener system comprised of at least two emulsifiers as described above; and combining a hydroalcoholic solvent with the thickener system at a temperature sufficient to melt said thickener system and in an amount that provides a composition having between at least about 0.5% and 8.0% by weight thickener system.

This invention also provides a method of preparing a stable hydroalcoholic composition comprising the steps of: (a) heating a thickener system to a temperature sufficient to melt said thickener system, wherein the thickener system is comprised of at least two emulsifiers as described above; (b) combining the thickener system and an aqueous phase, and (c) adding a lower chain alcohol to the aqueous/thickener system combination wherein the alcohol to water weight ratio in the composition is between about 35:65 to 100:0 and the thickener system is present in the composition between at least about 0.5% and 8.0% by weight.

DEFINITIONS

"Ambient temperature" as used herein refers to the temperature range between about 21 and 25 degrees C.

"Auxiliary thickeners" as used herein refers to additives (other than the emulsifiers which comprise the thickener system described below) which increase the viscosity of the solvent phase even in the absence of the thickener system. Certain auxiliary thickeners may act synergistically with the thickener system to increase the viscosity of the resultant formula. Auxiliary thickeners include but are not limited to soluble and swellable polymers and associative colloidal thickeners such as silica, magnesium aluminum silicate, and the like.

"Emollient" as used herein refers broadly to materials which are capable of maintaining or improving the moisture level, compliance, or appearance of the skin when used repeatedly.

"Emulsifier" as used herein is synonymous with "surfactant" and refers to molecules comprising hydrophilic (polar) and hydrophobic (non-polar) regions on the same molecule.

"Emulsion" as used herein refers to a stable dispersion of one liquid in a second immiscible liquid.

"Lotion" means liquid or cream, free of any propellant.

"Melt temperature" (Tm) as used herein refers to the temperature at which compositions or emulsions of the present invention dramatically lose viscosity.

"Polymer" as used herein refers to a natural or synthetic molecule having repetitive units and a number average molecular weight of at least 20,000.

"Solvent", "solvent system" or "hydroalcoholic solvent" as used herein refer to the alcohol and water combination in the present invention.

"Stable" as used herein refers to a composition that displays less than or equal to 10% by volume separation after centrifuging at 2275× g for 30 minutes at ambient temperature.

"Surfactant" as used herein is synonymous with "emulsifier," the definition of which is given above.

"Thickener system" as used herein refers to a combination of at least two emulsifiers each present in a concentration of at least 0.05% by weight capable of providing a viscosity of at least 4,000 centipoise at 23° C. to the compositions of the present invention without auxiliary thickeners.

DETAILED DESCRIPTION OF THE INVENTION

The invention provides a composition comprised of a lower chain alcohol, water, and thickening system. Alcohols used in the present invention are first discussed followed by a discussion of thickening systems. Ingredients which are optionally added to the composition such as antimicrobial agents and emollients are then discussed followed by a discussion of how to prepare compositions of the present invention.

Alcohol

The alcohol used in the present invention is a lower hydrocarbon chain alcohol such as a C1–C4 alcohol. In preferred embodiments the alcohol is chosen from ethanol, 2-propanol, or n-propanol, and most preferably ethanol. Ethanol is a preferred alcohol since it provides broad spectrum and quick killing of microbes and has an odor acceptable to consumers such as doctors, nurses and clinicians. The invention anticipates that a single alcohol may be used or that a blend of two or more alcohols may comprise the alcohol content of the composition.

The alcohol to water ratio in the present invention is between about 35:65 and 100:0 by weight. Compositions having alcohol to water ratios within the range 40:60 and 95:5 range ensure an efficacious immediate bacterial kill. In a preferred embodiment the alcohol:water ratio is between about 50:50 and 85:15, more preferably between about 60:40 and about 75:25, and most preferably the alcohol:water ratio is between about 64:36 and 72:28 by weight. Higher alcohol to water ratios are used in a preferred embodiment for optimum antimicrobial activity and to ensure the composition is fast drying.

Thickener System

The thickener system useful in this invention affects the cosmetic attributes of the final composition. Preferably, hand preps and lotions of the invention have the following desirable cosmetic attributes. The composition should not result in excessive clumping of glove powder beneath powdered surgical gloves and should not affect the integrity of the glove material. The composition should maintain an acceptable viscosity at 25° C. and preferably up to 35° C. Finally, in most the preferred embodiments formulations are stable to heat and cool cycles (heating up to 50° C. or higher and cooling to ambient temperature) as well as freeze/thaw cycles (cooling to −30° C. and warming to ambient temperature). All of these cosmetic attributes are affected by the types and amounts of emulsifiers chosen which comprise the thickener system of the present invention and are discussed below.

The thickener system of the invention must be compatible with the hydroalcoholic solvent system described above in order to provide acceptable cosmetic properties and appropriate viscosity. Compositions of this invention have a viscosity of at least about 4,000 cps at 23° C., preferably at least about 10,000 cps, more preferably at least about 20,000, even more preferably at least about 50,000 cps, even more preferably at least about 100,000 cps, and most preferably about 80,000 to about 500,000 cps measured using a very low shear viscometer such as Brookfield LVDV-I+ viscometer and T spindles with a heliopath adapter. Since the emollient system and other optional ingredients may affect the viscosity (either positively or negatively), the measured viscosity is that of the final composition without any added auxiliary thickeners.

The viscosity of the present invention is imparted by a thickener system comprised of at least two emulsifiers, and preferably at least two emulsifiers from different classes. In a preferred embodiment at least one of the emulsifiers is a solid at room temperature comprising at least one long chain hydrocarbon of at least 16 carbon atoms, preferably at least 18 carbon atoms, and more preferably at least 22 carbon atoms. At lower alcohol:water ratios of greater than 6:40 the long chain hydrocarbon preferably has greater than 22 carbon atoms. The thickener system of the present invention can be described in terms of the number average chain length of greater Man about 22 carbon atoms.

Emulsifiers of this invention are comprised of molecules having hydrophilic (polar) and hydrophobic (non-polar) regions on the same molecule and conform to the general structure:

$(R)_a(L)_b$

Where "R" represents a hydrophobic group, "L" represents a hydrophilic group, and "a" and "b" are independently 1 to 4.

In this invention "R" comprises an alkyl group of at least 16 carbon atoms, preferably at least 18 carbon atoms and more preferably at least 20 carbon atoms and most preferably at least about 22 carbon atoms; alkenyl group of at least 16 carbon atoms, preferably at least 18 and most preferably at least 20 carbon atoms; or aralkyl or aralkenyl group of at least 20 carbon atoms, preferably at least 24 carbon atoms and most preferably at least 26 carbon atoms. In a preferred embodiment R is unbranched.

In the above formula, "L" represents a hydrophllic group. For example, L can include an amide group having the structure —NHC(O)R'" or —C(O)NHR'" where R'" is hydrogen or an alkyl group of 1–10 carbon atoms optionally substituted in available positions by N, O, and S atoms; an ester group of short chain alcohols or acids (e.g., L=—C(O)OR' or —OC(O)R' where R' is C1–C4 branched or straight chain alkyl optionally substituted in available positions by hydroxyl groups); a polyglucoside group having 1–10 glucose units and more preferably 1–3 glucose units; a polyglycerol ester group having 1–15 glycerol units, preferably 2–12 glycerol units, and more preferably 3–10 glycerol units; a secondary amine group; a tertiary amine group; and a quaternary amine group.

"L" can also include an anionic group such as a sulfate, sulfonate, phosphate, phosphonate, or carboxylate group, or a zwitterionic group having the formula:

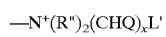

or

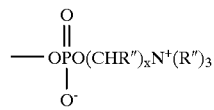

wherein each R" is independently hydrogen or an alkyl group (having 1–5 carbon atoms) or alkenyl group (having 2–4 carbon atoms), which alkyl or alkenyl groups are optionally substituted with nitrogen, oxygen, or sulfur atoms, including alkyl or alkenyl carboxyl groups; Q is hydrogen or hydroxyl; x is 1 to 4; and L' is —CO$_2^-$, —OP(O)(O$^-$)(O$^-$M$^+$), —(O)P(OR'")(O)(O$^-$M$^+$) (where R'" is hydrogen or an alkyl group of 1–10 carbon atoms optionally substituted in available positions by N, O, or S atoms), —SO$_2$O$^-$, or —OSO$_2$O$^-$, where M$^+$ is a positively charged counterion present in a molar ratio necessary to achieve a net neutral charge on the emulsifier and is selected from the group of hydrogen, sodium, potassium, lithium, ammonium, calcium, magnesium, or N$^+$R"$_4$.

"L" can also include an alcohol group; polyhydric alcohols such as, but not limited to, ethylene glycol, propylene glycol, butylene glycol, pentaerythrytol, glycerol, and sorbitol on ethylene oxide and/or propylene oxide group, preferably group having 2–150 moles of ethylene oxide plus propylene oxide per mole of hydrophobe ("R"), which is bonded to the hydrophobe through an ether or ester linkage, and optionally terminated by C1–C36 alkyl ester, C2–C36 alkenyl ester, or C6 to C36 alkaryl ester (i.e. aralkyl ester); an ester or ether group of a polyhydric alcohol and their polyalkoxylated derivatives; an ester or ether of sorbitan or polyalkoxylated (i.e., polyalkyleneoxide) sorbitan group preferably having 2–150 moles of alkylene oxide per mole of hydrophobic group, as well as combinations of these groups, e.g., a polyethoxylated polyglucoside group. Thus, it will be understood by one of skill in the art that the emulsifiers can include combinations of all "L" hydrophilic groups described herein (e.g., ester groups and amide groups in one molecule).

The hydrophobic and hydrophilic groups on non-ionic emulsifiers are generally selected to have a hydrophile/lipophile balance (HLB) of 2 to 20 and more preferably 4 to 16. Furthermore, the weight average HLB of the thickener system is preferably 4 to 16 and more preferably 8 to 12. (For example, a thickener system comprised of 40% by weight of an emulsifier with an HLB of 10 and 60% by weight of an emulsifier with an HLB of 15 has a weight average HLB of 13.)

The emulsifiers which comprise thickener systems may be chosen from a single class of surfactants (e.g., a mixture of chain length alkyl polyglucosides) but is preferably a mixture of emulsifier classes. Many commercially available emulsifiers are actually comprised of a mixture of chain lengths. For example, some behenyl alcohol as commercially supplied is actually a mixture of alcohols consisting of primarily C22 and C20 fractions but contain detectable levels of C24, C18 and C16 fractions. For this reason, the chain lengths specified herein refer to the number average chain length. Furthermore, in multiple emulsifier thickener systems of the present invention, each emulsifier must be present in a concentration of at least about 0.05% and more preferably at least about 0.1% by weight to be considered a component of a thickener system. Thickener systems of the present invention are capable of achieving high viscosities at relatively low total emulsifier concentrations. The total concentration of emulsifiers present as a thickener system is generally less than about 8% by weight, preferably less than about 5% by weight, more preferably less than about 4% by weight, and most preferably less than about 3% by weight of the total composition of the present invention. Typically, the thickener system is present in the composition in an amount of at least about 0.5% by weight, based on the total weight of the composition. In the most preferred compositions of this invention, the thickener system comprises between about 0.75% by weight to about 5% by weight, more preferably between about 1.0% by weight to about 3.5% by weight and most preferably between about 1.5% by weight to about 3% by weight of the composition. As used herein an emulsifier is considered part of the thickener system if its presence in the formula results in an increase in the viscosity of the composition. If a certain emulsifier does not result in increasing the viscosity of the composition, it is considered an emollient or stabilizer as defined below.

Preferred compositions of the present invention which are substantially free of polymeric thickening agents have a "melt temperature" (Tm). If compositions are heated above this melt temperature, they dramatically lose viscosity. The compositions of the present invention preferably have melt temperatures greater than 25° C. in order to maintain a high viscosity at room temperature. More preferably the melt temperature is greater than 35° C. in order to maintain viscosity once applied to the skin. The most preferred formulations have a melt temperature greater than 40° C. in order to allow shipping and handling without refrigeration. Thickener systems affect the melt temperature of a given composition. In order to obtain a preferred melt temperature a preferred thickener system includes at least one emulsifier which is solid at ambient temperature. Preferably, all emulsifiers of a thickener system are solid at ambient temperature to increase the melt temperature of the resultant composition.

The structure of emulsifiers in a thickener system affects the melt temperature of the resultant composition. In a preferred embodiment at least one emulsifier in a thickener system is capable of promoting a crystalline structure. Crystallinity is promoted by long straight chain alkyl groups, therefore, at least one emulsifier preferably comprises a saturated straight chain hydrocarbon of at least 16, preferably at least 18 and most preferably at least 20 carbon atoms. Certain hydrophilic head groups have been found to particularly promote association and crystallization. Suitable crystalline emulsifiers include alkyl alcohols, alkyl polyglucosides, polyglycerol alkyl esters, C1–C4 esters of alkyl alcohols, C1–C4 esters of alkyl carboxylates, optionally substituted alkyl amides, alkyl betaines and alkyl phosphates or phospholipids, alkyl quaternary amines, alkyl amine oxides polyethoxylated alkyl alcohols and alkyl esters of polyethylene glycol.

In addition to affecting the melt temperature of a composition, the emulsifier chain length also helps to determine the maximum level of ethanol which can be used in the composition and the concentration of emulsifiers required in the thickener system. At higher levels of alcohol, longer chain emulsifiers are required to produce viscous stable emulsions. It is believed that higher levels of alcohol tend to swell or solubilize the emulsifiers to a greater degree than lower levels of alcohol. Therefore, as the concentration of ethanol increases the chain length of the hydrocarbon chains in a thickening system must also increase in order to maintain a melt temperature over 35° C. That is, the amount of lower alcohol in the hydroalcoholic system can affect the choice of surfactant (i.e, emulsifier), and vice versa. For example, if the composition includes a lower alcohol to water ratio in excess of about 50:50, the thickener system should include at least one surfactant having a number average chain length of at least 16 carbon atoms. If the composition includes a lower alcohol to water ratio in excess of about 60:40, the thickener system should include at least one surfactant having a number average chain length of at least 18 carbon atoms. If the composition includes a lower alcohol to water ratio in excess of about 64:36, the thickener system should include at least one surfactant having a number average chain length of at least 20 carbon atoms.

For example, systems based on a C16/C18 alkyl polyglucoside (Montanov 68 available from Seppic, Inc. of Fairfield, N.J.) in combination with a C18 polyethoxylate (Brij 76 available from ICI of Wilmington, Del.) in 68:32 ethanol:water have a melt temperature of approximately 35° C. Similar systems having C22 hydrocarbon chains have melt temperatures of 45° C. or higher. In addition, as the chain length of the hydrophobic component in the thickener system increases, the amount of emulsifier required to achieve a certain viscosity decreases. For example, the Montanov 68 (C16/C18 alkyl polyglucoside)/Brij 76 (polyethoxylated C18 alcohol) thickener system requires approximately 5% total emulsifier to achieve a suitable viscosity. A similar system based on C22 hydrophobes achieves a suitable viscosity at only 2% total emulsifier.

The nature and size of hydrophilic head groups of emulsifiers are important and help to determine which thickening systems produce viscous stable systems. Certain combinations of emulsifiers will produce viscous stable emulsions. Without being bound by theory, it is believed that the size, charge, and degree of hydrogen bonding are important parameters to determine how emulsifiers interact.

Many preferred thickener systems are capable of producing viscoelastic compositions which are very stable. By varying the ratio of emulsifiers, the degree of elasticity can be adjusted from almost a purely viscous composition to a highly elastic and even stringy composition. If emollients are added, increasing the elasticity of the system imparts added stability to prevent separation of immiscible emollients. Excessive elasticity, however, is not preferred since an elastic composition usually does not provide a cosmetically appealing product. Addition of certain emulsifiers with at least two hydrophobic components has been shown to limit the viscoelasticity while ensuring viscous stable compositions. A favored class of multiple hydrophobic component emulsifiers are quaternary ammonium salts conforming substantially to the following structure:

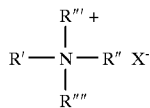

where: R' and R" are long chain alkyl or alkenyl hydrocarbon chains of at least 16 carbon atoms;

R'" is a short chain alkyl group of 1 to 4 carbon atoms, preferably methyl or ethyl;

R'''' is equivalent to either R' or R" and is preferably equivalent to R'"; and

X is a halogen, $R'''SO_3-$, $R'''SO_4-$, or $R'''CO_2-$

Some preferred structures include distearyldimethylammonium chloride, dibehenyldimethylammonium chloride, and dibehenyldimethylammonium methosulfate, while dibehenyldimethylammonium methosulfate is a more preferred structure. Other suitable multiple hydrophobic emulsifiers include dialkylglycerol esters, trialkylglycerol esters, polyglycerol alkyl esters, ethylene glycol dialkylesters, polyethylene glycol diallylesters, dialkylamides of diamines such as ethylene diamine, polyalkylesters of pentaerythritol and dialkyl (optionally ethoxylated) phosphates, and alkyl esters of polyethyoxylated alkyl alcohols.

The following emulsifier classes are offered as nonlimiting examples of suitable emulsifiers for use in the present invention. Examples of some preferred emulsifiers are provided for each emulsifier class. For the present invention an emulsifier must be present with at least one coemulsifier to provide a thickener system to produce stable viscous compositions.

Class 1. Alkyl or Alkenyl Polyglucosides:

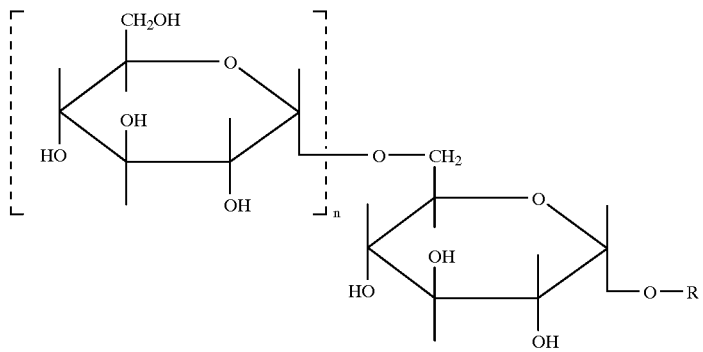

where R is a straight chain alkyl or alkenyl group of at least 16 carbon atoms, preferably at least 18 carbon atoms, and most preferably at least 20 carbon atoms; or an aralkyl or aralkenyl group of at least 22 carbon atoms, preferably at least 24 carbon atoms and most preferably at least 26 carbon atoms; and n=0–10 (when n=0, the valence of the oxygen atom is completed by H), preferably 1–5 and more preferably 1–3.

Nonlimiting examples of preferred alkyl or alkenyl polyglucoside emulsifiers include cetearyl glucoside sold as "MONTANOV" 68 by Seppic, Inc. of Fairfield, N.J.; behenyl glucoside, produced experimentally as "ESSAI 624" MP, an alkyl polyglucoside prepared with 92% C-22 alcohol and corn-derived glucoside by Seppic, Inc.; and oleyl glucoside.

Class 2. Short Chain Esters of long chain Alcohols or Acids:

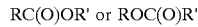

RC(O)OR' or ROC(O)R' where R is as defined immediately above for Emulsifier Class 1; and R' is C1–C4 branched or straight chain alkyl group, optionally substituted in available positions by hydroxyl groups.

Some preferred short chain esters of long chain alcohols or acids include but are not limited to methyl behenate sold as "KEMESTER 9022" by Witco, Humko Chemical Division of Memphis, Tenn.; methyl stearate sold as "KEMESTER 4516" by Witco; methyl oleate sold as "KEMESTER 205" by Witco; arachidyl proprionate available as "WAXENOL 801" from Alzo of Sayreville, N.J.; behenyl lactate, stearyl acetate; and glycerol monoerucate available from Croda, Inc. of Parsippany, N.J.

Class 3. Alkyl and Alkenyl Alcohols:

$R_6-OH$ where $R_6$ is a straight or branched chain alkyl or alkenyl hydrocarbon chain of at least 16 carbon atoms, preferably at least 18, more preferably at least 20 carbon atoms, and most preferably at least 22 carbon atoms, optionally substituted in available positions by N, O, or S atoms; or an aralkyl or aralkenyl group of at least 22 carbon atoms, preferably at least 24 carbon atoms and most preferably at least 26 carbon atoms optionally substituted in available positions by N, O, and S atoms.

Nonlimiting examples of preferred alkyl and alkenyl alcohol emulsifiers useful in a thickener system of the invention include stearyl alcohol available as "LANETTE 18" from Henkel's Emery Division of Cincinnati, Ohio; behenyl alcohol available as "LANETTE 22" from Henkel; oleyl alcohol available as "NOVOL" from Croda; C-24 alcohol available as "UNILIN 350" from Petrolite of Tulsa, Okla.; C31 alcohol available as "UNILIN 425" from Petrolite; and arachidyl alcohol available as "AR-20" from M. Michel and Co. of New York, N.Y.

4. Polyglycerol Ester

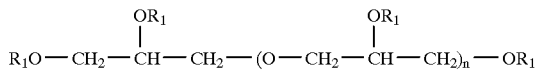

where each $R_1$ is independently hydrogen or a straight chain alkyl group of at least 16 carbon atoms, preferably at least 18 and more preferably at least 20 carbon atoms; or an aralkyl or aralkenyl group of at least 22 carbon atoms, preferably at least 24 carbon atoms, and most preferably at least 26 carbon atoms; and n =0 to 15, preferably 1 to 12, and most preferably 2 to 10.

Some examples of preferred polyglycerol ester emulsifiers useful in a thickener system of the present invention include but are not limited to decaglycerol monostearate available as "POLYALDO 10-1-S" from Lonza Inc. of Fairlawn, N.J.; tetraglycerol monostearate available as "TETRAGLYN 1-S" from Barnet Products Corporation of Englewood Cliffs, N.J.; and decaglyceroltetrabehenate.

Class 5. Quaternary Amine

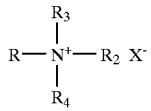

where R is as defined above in Emulsifier Class 1; $R_2$ is the same as $R_3$ or a long chain alkyl or alkenyl hydrocarbon chain of at least 16 carbon atoms, preferably at least 18 and more preferably at least 20 carbon atoms optionally substituted in available positions by N, O, and S; or an aralkyl or aralkenyl group of at least 22 carbon atoms, preferably at least 24 carbon atoms, and most preferably at least 26 carbon atoms;

$R_3$ is a short chain alkyl group of 1 to 4 carbon atoms, preferably methyl or ethyl; $R_4$ is equivalent to either $R_2$ or $R_3$ and is preferably equivalent to $R_3$; and X is a halogen, $R_5SO_3^-$, $R_5SO_4^-$, $R_5CO_2^-$, $(R_5)_2PO_4^-$, or $(R_5)PO_4^-$; where $R_5$ is defined in Class 6 below.

Nonlimiting examples of quaternary amine emulsifiers include dibehenyldimethylammonium methosulfate available as "INCORQUAT DBM-90" from Croda; behenyltrimethylammonium chloride available as "NIKKOL CA-2580" from Barnet; and tallowtrimethylammonium chloride available as "ARQUAD T-27W" from Akzo Chemicals, Inc. of Chicago, Ill.

Class 6. Tertiary Amine and its Protonated Salts

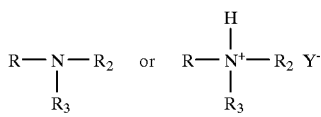

where R, $R_2$, and $R_3$ are as defined above in Class 5 and $R_2$ and $R_3$ may also be selected from polyethoxylated or polyproxylated alkyl or alkenyl alcohol chains having 1–50 moles of ethylene oxide or propylene oxide groups per mole of emulsifier and Y is a halogen, $R_5SO_3$—, $R_5SO_4$—, $R_5CO_2$—, $(R_5)PO_4^-$, or $(R_5)PO_4^-$, where $R_5$ is an alkyl or alkenyl group of 1–22 carbon atoms optionally substituted in available positions by N, O, and S.

Some examples of emulsifiers from the class of tertiary amines and their protonated salts useful in a thickener system of the invention include but are not limited to behenamidopropyldimethylamine available as "INCROMINE BB" from Croda; behenamidopropyldimethylamine gluconate; tallowdimethylamine hydrochloride; dihydrogenated tallow methyl amine; stearyl diethanolamine hydrochloride; polyethoxylated stearyl diethanolamine hydrochloride.

Class 7. Amine Oxides

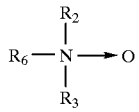

where $R_2$ and $R_3$ are as defined above for Class 6 and $R_6$ is as defined above for Class 3.

Nonlimiting examples of emulsifiers from the class of amine oxides suitable in a thickener system of the invention include behenamine oxide (behenyldimethylamine oxide) available as "INCROME B-30P" from Croda; stearamine oxide available as "INCROMINE Oxide S" from Croda; behenamidopropyldimethyl amine oxide; and bis(2-hydroxyethyl)tallow amine oxide available as "AROMOX T/12" from Akzo.

Class 8. Ethyoxylated and/or Propoxylated Alcohols and Esters and Derivatives thereof

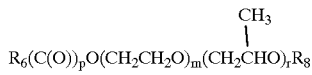

where $R_6$ is as defined above for Emulsifier Class 3; m=0–200, preferably 2–50, most preferably 4–20; p=0 or 1;

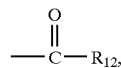

where $R_{12}$ is an alkyl or alkenyl group of 1–36 carbon atoms optionally substituted by N, O or S, or an aralkyl group of 6 to 36 carbon atoms; and
r=0–50.

Some examples of preferred emulsifiers from the class of polyethoxylated alcohols and esters include but are not limited to steareth-2 available as "BRU 72" from ICI Americas Inc. of Wilmington, Del.; steareth-10 available as "BRIJ 76" from ICI; beheneth-5 available as "NIKKOL BB-5" from Barnet Products Inc.; beheneth-10 available as "NIKKOL BB-10" from Barnet; C31 alkyl-IOEO available as "UNITHOX 450" from Petrolite Corp. of Tulsa, Okla.; C31 alkyl-40 EO available as "UNITHOX 480" from Petrolite, and the lauric ester of "UNITHOX 480" available from Petrolite as X-5171.

Class 9. Zwitterionics:

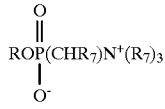

wherein R is as defined above for Emulsifier Class 1; each $R_7$ is independently hydrogen or an alkyl group (having 1–5 carbon atoms) or alkenyl group (having 2–4 carbon atoms), which alkyl or alkenyl groups are optionally substituted with nitrogen, oxygen, or sulfur atoms, including alkyl or alkenyl carboxyl groups; Q is hydrogen or hydroxyl; x is 1 to 4; and L' is —$CO_2$—, —OP(O)($O^-$)($O^-M^+$), —(O)P(OR''')(O)($O^-M^+$) (where R''' is hydrogen or an alkyl group of 1–10 carbony atoms optionally substituted in available positions by N, O, or S atoms) —$SO_2O^-$, or —$OSO_2O^-$, where $M^+$ is a positively charged counterion present in a molar ratio necessary to achieve a net neutral charge on the emulsifier and is selected from the group of hydrogen, sodium, potassium, lithium, ammonium, calcium, magnesium, or $N^+R'_4$ where each R' is independently an alkyl group of 1 to 4 carbon atoms optionally substituted with N, O, or S atoms.

Nonlimiting examples of emulsifiers from the class of zwitterions useful in the emulsifier system of the invention include stearamidopropylPG-dimmonium chloride phosphate available as "PHOSPHOLIPID SV" from Mona Industries of Paterson, N.J.; and behenyl betaine available as "INCRONAM B-40" from Croda.

Class 10. Alkyl and Alkenyl Amides:

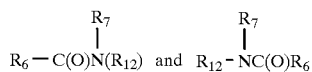

where $R_6$, $R_7$, and $R_{12}$ are as defined above in Classes 3, 9, and 8 respectively.

Examples of some preferred emulsifiers from the class of alkyl and alkenyl amides useful in a thickener system of the invention include but are not limited to behenamide available as "KEMAMIDE B" from Witco; stearamide available as "UNIWAX 1750" from Petrolite; Behenamidopropyldimethyl amine available as "INCROMINE BB" from Croda; stearyldiethanolamide available as "LIPAMIDE S" from Lipo Chemicals Inc. of Paterson, N.J.; and Erucamide available as "ARMID E" from Akzo.

Class 11. Esters and Ethers of Polyhydric Alcohols

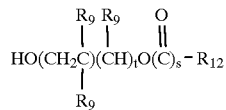

wherein t=0–4; each $R_9$ is independently chosen from H, —$CH_2OR_{10}$, —OH, or a hydrocarbon chain of 1 to 4 carbon atoms, preferably containing 1 carbon atom; s=0 or 1; wherein $R_{10}$=H or $R_{12}$ wherein $R_{12}$ is as defined above for Emulsifier Class 8.

Examples of esters and ethers include glycerol monobehenate, pentaerythritol distearate and glycerol tribehenate.

Esters and ethers of polyethoxylated polyhydric alcohols are also useful. For example, these include but are not limited to polyethoxylated glycerol monostearate, polyethoxylated penta erythritol behenate, polyethoxylated propylene glycol monostearate.

Class 12. Anionics

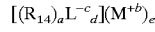

Where $R_{14}$ is an alkyl, alkenyl, or aralky group of at least 16 carbon atoms, preferably at least 18 carbon atoms and most preferably at least 20 carbon atoms optionally comprising oxygen, nitrogen, or sulfur atoms within or substituted upon the alkyl or alkenyl chain; or a polyethoxylated and/or polypropoxylated alkyl, alkenyl or aralkyl group, which alkyl, alkenyl, or aralkyl group comprises at least 16 carbon atoms, preferably at least 18 carbon atoms and most preferably at least 20 carbon atoms optionally comprising oxygen, nitrogen, or sulfur atoms within or substituted upon the alkyl, alkenyl, or aralkyl chain. When $R_{14}$ comprises a polyethoxylated or polypropoxylated substituent or a copolymeric substituent of ethylene oxide and propylene oxide, these subunits are present in amounts of 1 to 100 moles, preferably 1 to 20 moles per mole of hydrophobe; L is sulfate (—$OSO_2O^-$), sulfonate (—$SO_2O^-$), phosphate ((—$O)_2P(O)O^-$ or —$P(O)(O^-)_2$), or carboxylate (—$CO_2^-$; M is hydrogen ($H^+$), sodium ($Na^+$), potassium ($K^+$), lithium ($Li^+$), ammonium ($NH_4^+$), calcium ($Ca^{+2}$), magnesium ($Mg^+_2$), or $R''A^+$, wherein R'' is hydrogen or an alkyl or cycloalkyl group of about 1 to 10 carbon atoms, and $A^+$ is selected from the group consisting of $N^+(R)_3$ (e.g., $R''A^+$ can be $N^+(CH_3R)_4$, $HN^+(CH_2CH_2OH)_3$, $H_2N(CH_2CH_2OH)_2$) or a heterocyclic —$N^+B$ wherein B comprises 3 to 7 atoms selected from the group consisting of carbon, nitrogen, sulfur and oxygen atoms which complete the nitrogen-containing heterocyclic ring and satisfy the valence on the nitrogen atom; and wherein R is the same as R'' and may also be substituted in available positions with oxygen, nitrogen or sulfur atoms;

a and c are independently 1 or 2;
b and d are independently 1, 2 or 3; and
e is equal to (c times d)/b.

Nonlimiting examples of preferred emulsifiers from the anionic class of emulsifiers suitable for use in a thickener system of the invention include behenic acid available as Croacid B from Croda, Inc.; stearyl phosphate available as Sippostat 0018 from Specialty Industrial Products, Inc. of Spartanburg, S.C.; and sodium stearate available from Witco.

Class 13. Sorbitan Fatty Acid Esters

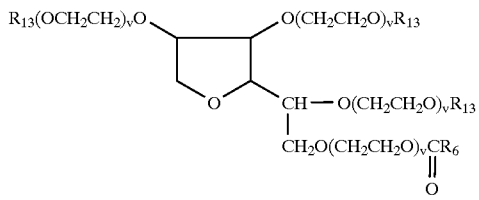

where $R_6$ is as defined above in Emulsifier Class 3, $R_{13}$ is H or

and each v is independently 0–30.

Fatty acid esters of sorbitan and its polyethoxylated derivatives, polyoxyethylene derivatives of mono and poly-fatty esters are also examples of additional emulsifiers useful in the present invention.

Certain combinations of the above-listed emulsifiers are useful in some preferred embodiments to form viscous stable thickener systems of the present invention. These preferred systems are listed below Nonlimiting Examples of Suitable Thickener Systems:

| System # | Emulsifier 1/(Class)* | Emulsifier 2/(Class)* | Emulsifier 3/(Class)* | Emulsifier 4(Class)* |
|---|---|---|---|---|
| 1 | alkyl polyglucoside (1) | polyethoxylated alkyl alcohol (8) | quaternary amine (5) | |
| 2 | alkyl polyglucoside (1) | polyethoxylated alkyl alcohol (8) | amine Oxide (7) | |
| 3 | alkyl polyglucoside (1) | tertiary amine (6) | | |
| 4 | alkyl polyglucoside (1) | quaternary amine (5) | | |
| 5 | polyglycerol ester (4) | polyethoxylated alkyl alcohol (8) | alkyl alcohol (3) | |
| 6 | polyglycerol ester (4) | polyethoxylated alkyl alcohol (8) | alkyl alcohol (3) | alkyl ester (2) |
| 7 | polyglycerol ester (4) | polyethoxylated alkyl alcohol (8) | quaternary amine (5) | |
| 8 | polyglycerol ester (4) | alkyl ester (2) | quaternary amine (5) | |
| 9 | polyglycerol ester (4) | amine oxide (7) | quaternary amine (5) | |
| 10 | alkyl/alkenyl alcohol (3) | alkyl ester (2) | quaternary amine (5) | |
| 11 | alkyl/alkenyl alcohol (3) | alkyl ester (2) | amine oxide (7) | |
| 12 | alkyl ester (2) | polyethoxylated alkyl alcohol (8) | quaternary amine (5) | |
| 13 | alkyl betaine (7) | polyethoxylated alkyl alcohol (8) | | |
| 14 | alkyl phospholipid (9) | polyethoxylated alkyl alcohol (8) | | |
| 15 | alkyl ester (2) | alkyl alcohol (3) | | dialkoxydimethicone |
| 16 | hydroxyfunctional ester (2) | polyethoxylated alcohol (8) | | |
| 17 | hydroxyfunctional ester (2) | alkyl alcohol (3) | quaternary amine (5) | |
| 18 | hydroxyfunctional ester (2) | quaternary amine (5) | | |
| 19 | polyglycerol ester (4) | polyethoxylated alkyl alcohol (8) | | |
| 20 | alkyl carboxylate (12) | polyethoxylated alkyl alcohol (8) | | |

*Refers to Emulsifier Classes identified above.

It is a simple matter to test certain combinations of emulsifiers to determine if they provide a suitable thickener system. Screening methodology is set forth in the Examples. The examples illustrate the importance of the head group size with respect to the ratio of the mixed emulsifiers required to produce a stable emulsion. For example, systems based on a C16/C18 alkyl polyglucoside combined with C18 polyethoxylates of varying level of ethoxylation (Brij) produce stable emulsions at widely varying ratios.

Without intending to be bound by theory, the physical structure of the composition of the invention is believed to be that of an emulsion. A classic definition of an emulsion is a stable dispersion of one liquid in a second immiscible liquid. However, as stated earlier, the present composition is preferably formed using at least one emulsifier which is a wax at room temperature. Although compositions of the present invention are not well characterized, they are believed to be a viscous stable mixture of a solid, semisolid, or liquid phase in a second liquid phase. It is believed that if certain hydrophobic emollients are added to the present invention, hydrophobic emulsifiers and immiscible emollients form an "oil" or hydrophobic phase which is dispersed in the hydroalcoholic liquid phase to form an "oil" in "water" emulsion. The hydroalcoholic phase is referred to herein as the "water" phase. Since many preferred emulsions are somewhat viscoelastic, these emulsions are believed to be liquid crystalline emulsions which have been cooled below the crystallization temperatures of the chosen emulsifiers to form a semi-crystalline gel-like network. Certain formulations may be simply swollen crystalline precipitates forming a strongly interacting network in the hydroalcoholic phase (so called coagel phase). The compositions of the present invention may also exist as combinations of these structures. Liquid crystalline and coagel phases in aqueous systems are described in "Application of Emulsion Stability Theories to Mobile and Semisolid O/W Emulsions," *Cosmetics and Toiletries* Vol. 101, pp 73–92 (1986), and "Influence of Long Chain Alcohols (or Acids) and Surfactants on the Stability and Consistencies of Cosmetic Lotions and Creams," *Cosmetics and Toiletries,* Vol. 92, pp. 21–28 (1977) both of which are hereby incorporated by reference. The exact type of molecular association that occurs depends on many factors including the nature, size, and physical and chemical states of the polar and hydrocarbon portions of the emulsifiers which comprise the thickener system at a specified temperature.

Emulsifiers other than those required in the composition to provide a thickener system may also be added as emollients or stabilizers. These emulsifiers are referred to herein as auxiliary emulsifiers. For example, certain emollients are also comprised of hydrophobic and hydrophilic regions and are useful in the present invention since they are believed to become incorporated into the liquid crystalline network. These emollients tend to enhance the stability of the composition as is discussed more fully below. Furthermore, certain dimethicone copolyol surfactants can actually improve the stability of formulations incorporating emollients. This is also discussed in more detail below.

Optional Ingredients

In addition to alcohol, water and thickener system, the compositions of the present invention may optionally include ingredients such as salts, emollients, stabilizers, antimicrobials, fragrances, therapeutic agents, propellants and additional emulsifiers. Each of these optional ingredients along with the effect each has upon the properties of the final composition is discussed below.

Salts

The melt temperature of the compositions of the present invention may be increased by adding salts. As the concentration of salt is increased, the ratio of emulsifiers will often need to change in order to maintain a stable composition. It is important to choose salts which do not create an unstable system and are compatible with any antimicrobials present in the system. For example, chlorhexidine digluconate (CHG) will precipitate rapidly in the presence of halide salts above a concentration of about 0.1M. Therefore, if a system includes CHG, preferably gluconate salts such as triethanolamine gluconate or sodium gluconate, are used.

Stabilizers

A stable composition is one which does not separate more than 10% by volume after centrifuging at 2275× g for 30 minutes as measured at the longitudinal midpoint of the sample tube. It is also recognized that stability may be time dependent due to crystallization of emulsifiers and/or emollients present in the system, coalescence of emollients, emulsifiers and the like and, therefore, preferred compositions do not exhibit separation of more than 10% after standing for 6 months at ambient conditions. Two types of stabilizers are useful in the present invention. These include (1) those stabilizers that complex with emulsifier hydrophilic head groups, and (2) those that associate with the emulsifier hydrophobic tails. Certain stabilizers may perform both functions. For example, emulsifiers comprising 1,2 diol-containing head groups such as alkylpolyglucosides, monoalkylglycerides, and polyglycerol alkyl esters, may be "stabilized" by adding borate ion. Without intending to be bound by theory, it is believed that borate ions complex with adjacent head groups which may increase the association of hydrophobic tails by holding them in close proximity. Natural or synthetic polymers comprised of pendent long chain alkyl groups (greater than 12 and preferably greater than 16 carbon atoms) such as stearyl modified cellulose derivatives, stearyl modified proteins such as wheat protein, stearyl modified collagen and the like are capable of stabilizing compositions of the present invention. Such added components may also increase the melt temperature of compositions of the present invention. It is believed that the pendent alkyl groups in these polymers associate by Van der Waals interactions with the hydrophobes of a thickening system, thereby enhancing the stability of the crystalline structure. Polymeric thickeners which do not have associative pendent alkyl chains may also increase the melt temperature presumably by increasing the viscosity of the continuous phase. A nonlimiting example of such thickeners are quaternary celluloses such as Celquat™ 230M as available from National Starch of Bridgewater, N.J. In a preferred embodiment stearyldimonium hydroxypropyl cellulose commercially available as Crodacel QS from Croda Inc., Parsippany, N.J. is added as a stabilizer.

Emollients

Emollients are typically added to hand lotions or hand preps because they act to increase the moisture content of the stratum corneum. Emollients are generally separated into two broad classes based on their function. The first class of emollients function by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants.

For the purposes of this invention the thickener system is considered separate and distinct from any emollients which may be added even though it is recognized that the emulsifiers may function as occlusive emollients and aid in maintaining or improving the skin condition. Emollients are included in a preferred embodiment of the invention and preferably comprise between about 3 and 30%, more preferably between about 4 and 20% and most preferably between about 5 and 12% by weight of the formulation.

The ratio of wax to liquid emollients (oils and humectants) in a preferred embodiment of the invention is between about 5:1 to 1:5 and preferably between about 1:3 to 3:1. Also, the ratio of wax emollients and wax emulsifiers to liquid emollients and liquid emulsifiers in a preferred embodiment of this invention is from about 1:5 to about 5:1, and more preferably, from about 1:3 to about 3:1. Emollients may be selected from any of the classes known in the art. A general list of useful emollients appears in U.S. Pat. No. 4,478,853 and EPO patent application 0 522 624 A1 and in the *CTFA Cosmetic Ingredient Handbook* published by The Cosmetic, Toiletry, and Fragrance Association, Wash. D.C. (1992) under the listings "Skin Conditioning agents," "emollients," "humectants," "miscellaneous" and "occlusive," each of these references is hereby incorporated by reference.

In preferred embodiments, emollients are chosen from the following nonlimiting list of general emollients, occlusive emollients and humectants. Examples of general emollients include short chain alkyl or aryl esters (C1–C6) of long chain straight or branched chain alkyl or alkenyl alcohols or acids (C8–C36) and their polyethoxylated derivatives; short chain alkyl or aryl esters (C1–C6) of C4–C12 diacids or diols optionally substituted in available positions by —OH; alkyl or aryl C1–C9 esters of glycerol, pentaerythritol, ethylene glycol, propylene glycol, as well as polyethoxylated derivatives of these and polyethylene glycol; C12–C22 alkyl esters or ethers of polypropylene glycol; C12–C22 alkyl esters or ethers of polypropylene glycol/polyethylene glycol copolymer; and polyether polysiloxane copolymers. In addition to many of the emulsifiers of preferred thickener systems, additional examples of occlusive emollients include cyclic dimethicones, polydialkylsiloxanes, polyaryl/alkylsiloxanes, long chain (C8–C36) alkyl and alkenyl esters of long straight or branched chain alkyl or alkenyl alcohols or acids; long chain (C8–C36) alkyl and alkenyl amides of long straight or branched chain (C8–C36) alkyl or alkenyl amines or acids; hydrocarbons including straight and branched chain alkanes and alkenes such as squalene, squalane, and mineral oil; polysiloxane polyalkylene copolymers, dialkoxy dimethyl polysiloxanes, short chain alkyl or aryl esters (C1–C6) of C12–C22 diacids or diols optionally substituted in available positions by OH; and C12–C22 alkyl and alkenyl alcohols. Nonlimiting examples of preferred humectant type emollients include glycerol, propylene glycol, dipropylene glycol, polypropylene glycol, polyethylene glycol, sorbitol, pantothenol, gluconic acid salts and the like.

Although a thickener system is responsible for the stability and overall consistency of compositions of the present invention, emollients may also affect the viscosity, stability, and melt temperature of a composition. It is anticipated that a single emollient may be added to the present invention or two or more emollients may be added to the composition. A wide range of emollients may be added to the formulations of the present invention. Preferably wax and oil type emollients along with water soluble emollients are used. In a preferred embodiment, emollient systems are comprised of humectants in addition to occlusive wax and oil emollients in concentrations which achieve a moisturizing but not greasy composition which maintains and improves the condition of the skin upon repeated use. Ideally, emollients are non-comedogenic and are chosen to ensure no skin irritation or sensitization reaction occurs. This is particularly critical since the composition of the present invention will likely be worn in an occluded condition under surgical gloves. Furthermore, emollients should be chosen which do not affect the integrity of the glove material. For example, since hydrocarbon emollients such as mineral oil and petrolatum can detrimentally affect the tear strength of surgical gloves, these emollients may need to be avoided for compositions employed as presurgical disinfectants.

Without being bound or limited by theory, it is believed that if emollients are added to the present compositions, they may be present in four distinct regions. The emollients could occur (1) as a soluble species in the solvent phase, (2) dispersed as emulsified droplets within the mixed emulsifier micelle or crystalline gel network, (3) incorporated into the mixed emulsifier micelle or crystalline gel network, or (4) as a separate and distinct emulsion. As earlier stated, emollients can affect the melt temperature of a composition. Those emollients that are soluble or dispersible in the solvent phase tend to have little or no affect on the melt temperature and are therefore preferred. These emollients include the humectant and general emollients. The most preferred general emollients are those which are essentially insoluble in water but soluble in the hydroalcoholic solvent. These emollients are also preferred since they remain soluble and uniformly dispersed even above the melt temperature so that upon cooling to room temperature a uniform composition results. In addition, they are also believed to have little effect on surgical gloves. Such general emollients typically do not have alkyl or alkenyl chains greater than about 14, preferably not greater than 12 and most preferably not greater than about 9 carbon atoms.

Those emollients which are insoluble in the hydroalcoholic solvent may associate with the emulsifiers of the thickener system and/or become incorporated into the micelle or crystalline gel network. Preferred emollients within this class are those emollients that are very hydrophobic since they tend to maintain a high melt temperature. For example, hexadecane was found to increase the viscoelasticity of certain thickener systems. Those emollients which are capable of associating with and disrupting the emulsifiers of the thickener system tend to decrease the melt temperature and may influence the stability of the composition. Certain branch alkyl esters of greater than about 12 carbon atoms per hydrophobe have been found to be particularly effective at decreasing the melt temperature. For example, trioctyldodecyl citrate has been found to significantly decrease the melt temperature of some systems.

Emollients which become incorporated into the thickener system tend to decrease the melt temperature. For example, laureth-4 (Brij 30) appears to incorporate into the thickener system since it does not phase out when heated above the melt temperature at concentrations below about 1% by weight. Laureth-4 also tends to decrease the melt temperature of the composition.

Certain emollients which are insoluble in the hydroalcoholic solvent can be emulsified in what is believed to be a separate and distinct emulsion. These emollients have little affect on the melt temperature of a composition. For example, certain cyclic silicones, polysiloxanes, and dialkoxypolysiloxanes can be emulsified in hydroalcoholic solvents using polyether/polysiloxane copolymers surfactants. Cyclic silicones such as DC344 (available from Dow Corning of Midland, Mich.) in the presence of certain polyether/polysiloxane copolymers such as Abil B88183 available from Goldschmidt Chemical Corp. of Hopewell, Va., can form a thermally stable emulsion such that the compositions remain uniform both above and below the melt temperature. In fact, the combination of a long chain dialkoxypolysiloxane and polyether/polysiloxane copolymer has been found to actually promote the stability of certain thickener systems. The dialkoxypolysiloxane is believed to interact with the thickener system as well as the polyether/polysiloxane copolymer. These compounds have the following structures:

Dialkoxy dimethicones $$R-O-Si(CH_3)_2-O[Si(CH_3)_2-O]_z-Si(CH_3)_2-OR$$

where R is a straight chain alkyl group of 14–50, preferably 16–24 carbon atoms, and z=5–300

Polyether/polysiloxane Copolymers (Dimethicone Copolyols):

$$(CH_3)_3-Si-O-[Si(CH_3)R_{11}-O]_x[Si(CH_3)R_8-O]_y-Si(CH_3)_3$$

where x+y=5–400, preferably 15–200, and $R_8$ is a polyether substituted alkyl group with the structure:

$$-R_9-O(C_2H_4O)_p(C_3H_6O)_qR_{10};$$

where $R_9$ is an alkyl group of 1 to 6 carbon atoms;

$R_{10}$ is hydrogen or an alky group of 1–22 carbon atoms;

$R_{11}$ is an alkyl group of 1 to 22 carbon atoms or phenyl;

p=2–300, preferably 8–100; and q=0–100.

Note that branched chain polysiloxanes modified as shown in the two structures above are also possible.

The following are nonlimiting examples of emulsifier/emollient components which improve thickening/stability of compositions of the present invention.

a. Certain wax emulsifiers/emollients have been found to be particularly useful and include solid waxy esters such as: Myristyl Myristate, Cetyl Palmitate, Myristyl Stearate, Stearyl Behenate, Behenyl Isostearate, Isostearyl Behenate, Behenyl Behenate, Lauryl Behenate, Behenyl Erucate. These have the following formula:

$$R_1-CO_2-R_2$$

where:

$R_1$ is at least 14 carbon atoms; and $R_2$ is an alkyl or alkenyl of at least 4 carbon atoms.

b. Long chain hydrocarbon di-esters, tri-esters, of polyhydric alcohols with melting point greater than 23° C. include solid esters such as glycerol tribehenate and sorbitan tristearate.

c. Pure lanolins and lanolin derivatives (e.g. hydrogenated lanolin) provide excellent emolliency but can also improve the stability of the emulsion when used in combination with oil emollients.

d. Petrolatums provide excellent emolliency and can also improve the stability of the emulsion when used in combination with oil emollients. Petrolatums are mixtures of oily and waxy long chain hydrocarbons.

e. Microcrystalline waxes and branched hydrocarbon waxes with a melting point greater than 50° C. and a molecular weight greater than 400. An example of this includes but is not limited to Vybar 103 which is a branched hydrocarbon with a number average molecular weight of 2800 and is available from Petrolite Corp. of Tulsa, Okla. and "ULTRAFLEX" which is a microcrystalline wax also available from Petrolite Corp.

f. Oxidized waxes and modified hydrocarbon waxes may find application in the present invention. These are prepared from waxes modified by oxidation, salts of oxidized waxes, maleic anhydride adducts of polyolefins and urethane derivatives of oxidized synthetic or petroleum waxes. Applicable waxes could include Petrolite's Cardis or Petronauba microcrystalline and polyethylene-based oxidized products, Polymekon (salts) and Ceramer (anhydride adducts).

g. Fully saturated homopolymers of polyethylene or copolymers of various alkene monomers may be used to form polymers with a molecular weight at or below 3,000 with a melting point below 130° C. and low melt viscosities. Applicable waxes could include "POLYWAX" available from Petrolite Corp.

Fragrances

The formulations may also comprise a fragrance. If fragrances are included the fragrances must be chosen carefully since some fragrances are known to cause skin irritation and/or sensitization reactions.

Antimicrobials

In addition to the lower alcohols present in the composition of the present invention, other antimicrobials may be added to enhance the antimicrobial action of the compositions of the present invention. This may be particularly desirable in critical uses such as presurgical hand scrubs or presurgical patient slin scrub replacements. Suitable additional antimicrobials include iodine and its complexed forms such as povidone/iodine, chlorhexidine salts such as chlorhexidine digluconate (CHG), parachlorometaxylenol (PCMX), hexachlorophene, phenols, surfactants comprising a long chain hydrophobe (C12–C22) and a quaternary group, triclosan, Lauricidin, quaternary silanes, hydrogen peroxide, silver, silver salts such as silver chloride, silver oxide and silver sulfadiazine and the like. In order to reduce chances for irritation and yet maintain efficacy, the antimicrobial level should be adjusted to the minimum level which maintains a low bacteriological count for 6 and most preferably for 12 hours after application.

The most preferred additional antimicrobial is chlorhexidine since it is capable of ensuring long term antimicrobial efficacy. If chlorhexidine is added to the present invention it is preferably present as a soluble salt. The diacetate and digluconate salts are preferred. The most preferred antimicrobial is chlorhexidine digluconate (CHG). CHG is preferably present at a concentration of 0.05–5.0%, more preferably from 0.1–3% and most preferably from 0.25–2% by weight. Chlorhexidine is a bis(diguanide) and therefore is very basic and is capable of forming multiple ionic bonds with anionic materials. For this reason, chlorhexidine-containing thickener system are preferably based on non-ionic and/or cationic emulsifiers. Certain zwitterionic, very insoluble, or non-precipitating anionic emulsifiers may also be useful.

Foams

The compositions of the present invention may also be formulated into an aerosol foam or mousse by addition of an appropriate propellant. The propellant must be chosen to ensure proper delivery from the container to prevent clogging of the valve. The propellant can be chosen from chlorofluorocarbons (CFCs), hydrochlorofluorocarbons (HCFCs), hydrofluorocarbons (HFCs), perfluorinated alkanes, and lower alkanes (C1–C5) as well as nitrous oxide dimethyl ether and other solvent-soluble propellants. Preferred propellants are lower alkanes such as propane, butane, and isobutane since these result in a dramatic loss in viscosity making the formulation easy to dispense. A 70/30 mixture of propane/isobutane is a particularly preferred embodiment. In order to produce an aerosol composition the antimicrobial lotion is first formulated and charged into an appropriate pressure rated container. If convenient, the formulation may be heated above the melt temperature in order to facilitate filling. The propellant is then added under pressure at approximately 2–30% preferably 3–20% by volume. The propellant may form a separate layer or may remain emulsified in the composition.

Alternate applications for hydro-alcoholic liquid crystalline solutions

The compositions of this invention may be compounded with UV absorbers and oils to deliver fast-drying sunscreens. Antimicrobials such as benzoyl peroxide may also be added to the formulations and the formulations may be useful as an acne medication. The systems of this invention may also be formulated with barrier compounds to form barrier creams and lotions. Materials which may be added to provide barrier protection for use as skin barriers to protect against diaper rash include but are not limited to 0.1 to 60% aldioxa, allantoin, aluminum acetate, aluminum hydroxide, bismuth subnitrate, boric acid, calamine, cellulose (microporous), cholecalciferol, cocoa butter, cod liver oil (in combination), colloidal oatmeal, cysteine hydrochloride, dexpanthenol, dimethicone, glycerin kaolin, lanolin (in combination), live yeast cell derivative, mineral oil, peruvian balsam, peruvian balsam oil, petrolatum, protein hydrolysate (1-leucine, 1-isoleucine, 1-methionine, 1-phenylalanine, and 1-tyrosine), racemethionine, shark liver oil, sodium bicarbonate, sulfur, talc, tannic acid, topical starch, vitamin A, white petrolatum, zinc acetate, zinc carbonate and zinc oxide. Formulations are also contemplated containing antifungal agents for treating fungal infections of the skin such as athlete's foot and the like.

A related patent application entitled, "Stable Hydroalcoholic Compositions," attorney docket number 51800 USA 7A, Ser. No. 08/493,695 filed on Jun. 22, 1995 abandoned by inventors Asmus, Scholz and Charpentier is hereby incorporated by reference.

Since many of the compositions of the present invention contain antimicrobials, it is important that they be dispensed in an efficacious and precise amount. The compositions of the present invention can be dispensed in a discreet, substantially uniform amount using the dispensers disclosed in Applicants' Assignee's Copending U.S. patent application Ser. Nos. 08/668,198, filed Jun. 21, 1996, entitled "Dispenser for Antimicrobial Liquids" and Ser. No. 08/668,270, filed Jun. 21, 1996, U.S. Pat. No. 5,799,841, entitled "Drip Resistant Nozzle for a Dispenser."

METHODS OF PREPARATION

The compositions of the present invention may be prepared by a variety of techniques. For example, the process can often be as simple as adding the thickener system to the hydroalcoholic solvent at a temperature above the melting point of the emulsifiers, mixing briefly and cooling. Nevertheless, to ensure a composition of maximum stability the components are preferably subjected to high shear (e.g. homogenized) for a limited time period while above the melting point of the thickener system followed by low shear mixing while cooling. The system should be mixed under high shear long enough to ensure a very small "droplet" size, however, excessive high shear mixing may result in decreased viscosity and stability.

The cooling rate may be important depending on the particular thickener system. Certain thickener systems can be homogenized and then allowed to cool slowly, however, rapid cooling appears beneficial for most systems.

The order of adding the components may also affect the stability and viscosity of the system. In general it works well to melt the mixed emulsifiers with aqueous-insoluble emollients together in one vessel. The hydroalcoholic solvent and any aqueous miscible emollients are mixed in a second vessel. Both components are heated above the melting temperature of the thickener system. The hot liquid components are mixed together rapidly followed by approximately 1 to 5 minutes of homogenization for typical batches under 500 grams. While still low in viscosity the system is stirred using moderate agitation and cooled. It is also possible to add the molten thickener system along with any solvent insoluble emollients to hot water (i.e., water at a temperature above the melting temperature) followed by high shear mixing and subsequent dilution with alcohol. The processing variables including amount and intensity of high shear mixing, rate of cooling, and order of addition are easily determined by one skilled in the art.

TEST METHODS

Viscosity

U.S. Pat. No. 5,799,841, In the following Examples (except where indicated) viscosity was measured at 23° C. at ambient pressure using a Brookfield LVDV-I$^+$ viscometer equipped with a model D Brookfield heliopath and T spindles B-F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20–80% of the viscometer range and more preferably between 30–70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The following table outlines preferred spindles for various sample viscosities.

| Sample Viscosity | T Spindle to Use |
|---|---|
| 1,000–100,000 | B |
| 10,000–200,000 | C |
| 50,000–500,000 | D |
| 100,000–1,250,000 | E |
| 500,000–3,000,000 | F |

The viscosity of each sample was taken as the highest relatively stable reading achieved on the first path the spindle traversed using the heliopath adapter.

Stability

The stability of samples was measured 24 hours after conditioning at ambient conditions by placing 12 ml of a formulation that formed a lotion/cream in a 15 ml graduated centrifuge tube. The tube was then centrifuged in a Labofuge B (Heraeus Sepatech GmbH, Model 2650, rotor 2150 and buckets #2101) at 3000 rpm (2275× g when measured at the longitudinal midpoint of the sample tube) for 30 minutes at 23° C. Stability is recorded as a volume percent separation in the Examples below.

Melt Temperature (Tm)

The melt temperature was measured by placing approximately 15 grams sample in a 25 cc sealed glass vial and placing the vial in a water bath. The temperature of the bath was increased periodically in discrete increments and the contents checked after approximately 1 hour at a given temperature. The melt temperature was taken as the temperature at which the mixture became very low in viscosity.

Minimum Inhibitory Concentration (MIC)

An overnight culture of *E. coli* ATCC 8739 (lab strain 223) and/or *S. Aureus* ATCC 14154 (lab strain 502) grown on trypticase soy agar plates was resuspended in Mueller-Hinton Broth to a cell density of 0.6–1.2×10$^6$ colony forming units per milliliter. Chlorhexidine samples were prepared by adjusting CHG to 512 μg/ml in Mueller-Hinton Broth and serially diluting in two-fold steps in Mueller-Hinton Broth. The CHG-containing Mueller-Hinton Broth was placed in 96-well sterile microliter plates and each well was inoculated with the bacteria. The plates were then incubated for 24–48 hrs at 37° C. Bacterial growth was determined visually by comparing the plates. The MIC was determined as the lowest concentration of CHG that resulted in complete kill of the test organism.

Cosmetic Properties/Tactile Testing

For use in presurgical disinfection the compositions of this invention are preferably formulated with emollients to achieve a moisturized but relatively dry feel. Lotions with excessive emollients tend to be perceived as greasy and can result in excessive clumping of the powder under surgical gloves. The formulations of this invention do not provide a tacky or sticky feel even in high humidity environments throughout the application process. The invention formulations preferably yield a smooth, soft, non-tacky, and moisturized feeling. Testing of the cosmetic or tactile properties of the compositions was conducted with preferably greater than ten evaluators who applied a premeasured amount of product, approximately 2 ml. Since hand washing can affect the feel of the compositions, evaluators washed thoroughly with Ivory Skin Cleansing Liquid Gel hand soap available from Procter and Gamble, Cincinnati, Ohio before applying the sample. After drying, the composition was rubbed uniformly over the surfaces of both hands until the composition was dry. The feel of the composition on the skin during subsequent washing with soap and water was also important. Approximately 30–60 min. after application of the composition the feel during subsequent washing was evaluated. Preferred formulations did not result in an abnormal feeling such as slimy, slippery, or sticky characteristics.

EXAMPLES

The following Examples are provided to illustrate the invention and are not intended to limit the scope of the invention.

Example 1: Alkyl Polyglucoside Thickener Systems

An alkyl polyglucoside emulsifier having an alkyl chain of 16 to 18 carbons was obtained as Montanov 68 from Seppic Inc. of Fairfield, N.J. This highly crystalline emulsifier was combined with other emulsifiers to form thickener systems in a hydroalcoholic solvent. The solvent was either 60:40 or 68:32 ethanol:water by weight. 200 proof ethanol and distilled water were used. The Montanov 68/co-emulsifier ratio was varied keeping the total emulsifier concentration fixed at 5% by weight according to the following table:

| Emulsifier | Formulation (grams) | | | |
| | A | B | C | D |
|---|---|---|---|---|
| Montanov 68 | 2 | 1.5 | 1 | 0.5 |
| Co-emulsifier | 0.5 | 1.0 | 1.5 | 2.0 |
| 60:40 ethanol:water | 47.5 | 47.5 | 47.5 | 47.5 |

Each co-emulsifier/Montanov 68 composition was prepared using the following procedure:

1. The emulsifiers were heated above their melting temperature to 75° C.

2. The hydroalcoholic solvent was heated to 75° C. in a sealed jar.
3. The hot hydroalcoholic solvent was rapidly added to the molten emulsifiers.
4. The mixture was homogenized at maximum speed for 4 minutes using a Silverson L4R homogenizer available from Silverson Machines, Waterside England.
5. The vessel was then immersed in 15–20° C. water with moderate agitation using an overhead paddle impeller for 20 minutes.

viscosity decreases. For example, within the ceteth series (Brij 52–58) the maximum viscosity is 240,000 cps for Ceteth-2 whereas Ceteth-20 had only a maximum viscosity of 60,000 cps. Similar results were found for the steareth series (Brij 72–78) and the beheneth series (Nikkol BB series).

Example 2: Alkyl Polyglucoside/Brij 72 Optimization

A series of 15 formulations were prepared using a three component mixture design based on the results of Example

| Emulsifier | Solvent | Formulation Viscosity (cps) and/or % Separation by Volume | | | |
|---|---|---|---|---|---|
| | | A | B | C | D |
| Nikkol BB-5 (beheneth-5) | 60:40 | 240,000 cps 0% separation | 2200 cps 0% | 29300 cps 0% | 26600 0% |
| Nikkol BB-5 (beheneth-5) | 68:32 | 1500 | 48000 | 57000 | 25000 |
| Nikkol BB-10 (beheneth-10) | 68:32 | 3400 | 17000 | 9300 | NS |
| Nikkol BB-10 (beheneth-20) | 68:32 | 32000 | 6800 | 450 | NS |
| Brij 52 (ceteth-2) | 60:40 | 950 | 240000 | 36000 | 43000 |
| Brij 58 (ceteth-20) | 60:40 | 56000 | 60000 | 770 | <100 |
| Brij 72 (steareth-2) | 60:40 | 470000 | 66000 | 48000 | 49000 |
| Brij 72 (steareth-2) | 68:32 | NS* | 1500 | 34000 | 14000 |
| Brij 76 (steareth-10) | 68:32 | 35000 | 14600 | 3100 | <100 |
| Brij 78 (steareth-20) | 60:40 | 294000 | 54000 | 6200 | 270 |
| Brij 78 (steareth-20) | 68:32 | 2700 | 1300 | 200 | NS |
| Unithox 420(C31 alkyl-2EO) | 68:32 | 730 | 850 | 600 | NS |
| Unithox 450(C31 alkyl-9.8O) | 68:32 | 600 | 770 | 17600 | NS |
| Incromine BB (behenmidopropyldimethyl amine) | 60:40 | NS | 3600 0% | 70000 <2% | 630 24% |
| Incromine BB | 68:32 | 6000 | 420 | 520 | NS |
| Incromine BB gluconate | 60:40 | 75 50% | 23000 0% | 1200 0% | 2000 5% |
| Armid 18 (octadecenamine) | 60:40 | <100 | NS | NS | NS |
| Lanette 18 (Stearyl alcohol) | 60:40 | NS | NS | NS | NS |
| Uniwax 1750 (stearamide) | 60:40 | NS | NS | NS | NS |
| Triton X-15 (octylphenol ethoxylate) | 68:32 | NS | NS | NS | NS |
| Triton X-35 (octylphenol ethoxylate) | 68:32 | NS | NS | NS | NS |

*NS = not stable

The results show that certain thickener systems form stable viscous compositions. Those thickener systems that form stable compositions have widely varying viscosities depending on the emulsifiers and the ratio of the alkylpolyglucoside to co-emulsifier. For example, mixtures of Montanov 68 and Brij 52 had viscosities which varied from 950 to 240,000 cps. This example also illustrates the effect alcohol:water ratio has on resulting stability and viscosity. For example, at an ethanol:water ratio of 60:40, the Montanov 68:Brij 72 system had a maximum viscosity of 470,000 cps at a weight ratio of 4:1 (formulation A). When the ethanol:water ratio was increased to 68:32 the 4:1 ratio was no longer stable and the maximum viscosity was only 34,000 cps at a weight ratio of 2:3 (formulation C). Similar shifts appear for the Montanov 68:Nikkol BB5 and Montanov 68:Brij 78. It appears that higher viscosities are achievable at lower alcohol levels presumably due to lower solubility of the emulsifiers and that peak viscosities appear at higher concentrations of Montanov 68 presumably due to the highly crystalline nature of alkyl polyglucoside emulsifiers.

The results also indicate that the size of the hydrophilic group influences the stability and viscosity even within the group of mixed emulsifiers which produce stable systems. For example, as the degree of ethoxylation increases, the hydrophilic group size increases and, in general, the peak 1. The following concentration ranges were investigated using a solvent ratio of 68:32 ethanol:water.

| Component | Percent by weight |
|---|---|
| Montanov 68 | 0.26–3 |
| Brij 72 | 1.0–5.2 |
| Solvent | 94–98 |

Each formulation was prepared and subsequently tested for stability and viscosity. The viscosities of the resulting formulations ranged from less than 50 cps to 93,600 cps. Stability results ranged from 0–83%. Examples of several optimized formulations appear below:

| Formula | Montanov 68 | Brij 72 | Solvent | Viscosity (cps) | Stability (% volume separation) |
|---|---|---|---|---|---|
| | Percent by weight | | | | |
| A | 0.26 | 5.20 | 94.54 | 65,000 | 3 |
| B | 3.00 | 3.00 | 94 | 93,600 | 0 |
| C | 2.20 | 2.92 | 94.88 | 72,000 | 0 |
| D | 2.20 | 1.92 | 95.88 | 30,000 | 0 |

-continued

| Formula | Montanov 68 | Brij 72 | Solvent | Viscosity (cps) | Stability (% volume separation) |
|---|---|---|---|---|---|
| E | 1.80 | 2.70 | 95.5 | 30,000 | 0 |
| F | 3.20 | 2.30 | 94.5 | 50,000 | 0 |

These results together with those of Example 1 indicate that the viscosity of the formula for this thickener system is dependent upon the ratio of the emulsifiers. The results also indicate that even when varying the ratio of the emulsifiers in thickener systems, high viscosities are still obtained while maintaining acceptable stability values. Furthermore, the total concentration of thickener system necessary to achieve a certain viscosity varies considerably depending on the ratio of emulsifiers. For example, Formula D had a viscosity of 30,000 cps with a total emulsifier concentration of only 4.12% by weight.

Example 3: Alkylypolyglucoside Ternary Thickener Systems

Based on the results obtained in Example 2, formulae E and F were chosen for use as base systems to which a third emulsifier was added to further increase the viscosity. The third emulsifier was added at concentrations of 0.3, 0.8, 1.3 and 1.8% by weight keeping the ratio of Montanov 68 and Brij 72 at the ratios found effective in formulations E and F of Example 2 according to the following table:

Formula

| Component | A | B | C | D | E | F | G | H |
|---|---|---|---|---|---|---|---|---|
| | \multicolumn{8}{c}{Amount (grams)} |
| Montanov 68 | 0.92 | 0.92 | 0.92 | 0.92 | 1.11 | 1.11 | 1.11 | 1.11 |
| Brij 72 | 1.37 | 1.37 | 1.37 | 1.37 | 1.55 | 1.55 | 1.55 | 1.55 |
| Coemulsifier | 0.15 | 0.40 | 0.65 | 0.90 | 0.15 | 0.40 | 0.65 | 0.90 |
| Solvent | 47.57 | 47.32 | 47.07 | 46.82 | 47.19 | 46.94 | 46.69 | 46.44 |

The solvent used was 68:32 ethanol:water. The formulations were prepared and subsequently tested for stability and viscosity. The third co-emulsifiers used were behenyl alcohol (Lanette 22, Henkel Corp.) and stearamide diethanolamine (Lipamide S, Lipo Chemical of Paterson, N.J.). The following viscosity results were found:

VISCOSITY (cps)

| Coemulsifier | A | B | C | D | E | F | G | H |
|---|---|---|---|---|---|---|---|---|
| Lipamide S | 42,500 | 70,500 | 82,800 | 111,000 | 75,500 | 120,000 | 91,100 | 90,000 |
| Lanette 22 | 59,100 | 88,800 | 93,600 | 92,300 | 14,500 | 62,000 | 86,800 | 81,600 |

All formulations had stability values of 0% separation except formula A/Lanette 22 which showed a trace (<5%) amount of separation. The results indicate that addition of a third emulsifier into the thickener system can increase the viscosity. The results also indicate that the length of the hydrocarbon on the third emulsifier does not necessarily predict viscosity. In this example, Lipamide S, although it has a significantly shorter hydrocarbon chain than Lanette 22, generally, produced higher viscosity compositions.

Example 4: Effect of Shear on Viscosity and Stability

Formulation C from Example 2 was used as a base system to test the effect of varying levels of shear on the resulting viscosity and stability of the compositions. The thickener and the solvent were heated to 75° C. in separate containers. The solvent was added to the emulsifiers rapidly and the composition mixed as described below:

A  hand shaken for less than 1 minute
B  hand shaken for less than 1 minute, sealed and placed on a roller for 4 hours at 50 rpm
C  stirred 20 minutes at low speed with an overhead stirrer
D  homogenized for 4 minutes, sealed and allowed to sit
E  homogenized for 2 minutes, stirred 10 minutes at low speed with an overhead stirrer
F  homogenized for 1 minute, stirred 10 minutes at low speed with an overhead stirrer
G  homogenized for 4 minutes, stirred 20 minutes at low speed with an overhead stirrer
H  homogenized for 4 minutes, placed on a roller for 3.25 hours at 50 rpm
I  homogenized for 4 minutes, placed on a roller for 50 minutes at 50 rpm A wide variety of consistencies resulted as indicated below:

| Formula | Appearance | Viscosity (cps) | Stability (% separation) |
|---|---|---|---|
| A | white, pearlescent, crystalline regions | 7,400 | 64 |
| B | opaque white cream | 1,290 | 0 |
| C | opaque, pearlescent, cohesive | 60,700 | 0 |
| D | bluish, transparent, pearlescent, cohesive | 27,600 | 0 |
| E | opaque, pearlescent, cohesive | 81,200 | 0 |
| F | opaque, pearlescent, cohesive | 85,500 | 0 |
| G | white, opaque, pearlescent, cohesive | 61,700 | 0 |
| H | bluish opaque, not cohesive | 995 | 0 |
| I | * | 27,000 | 0 |

*Appearance not recorded

The results indicate that for this thickener system the intensity and degree of mixing have an affect on the resultant product. Both too little mixing (Formula A) and too much mixing (Formula H) had deleterious affects on the viscosity. A preferred method of mixing is a combination of brief (1–2 minutes) high shear homogenization followed by overhead stirring for 10 minutes (Formulae E and F).

Example 5: Effect of Added Polymers

This example investigated the effects of adding various polymers ((1) polymers containing pendant alkyl groups and (2) linear and soluble in the solvent and (3) crosslinked and swellable in the solvent) to a thickener system. The polymers used were:

(1) Crodacel QS (Croda, Inc. of Parsippany, N.J.)— Stearyldimonium hydroxypropyloxyethyl cellulose
(2) Quatrisoft LM-200 (Amerchol Corp. Edison, N.J.) Lauryldimmonium modified hydroxyethylcellulose (CTFA Polyquaternium 24)

(3) Salcare 96 (Allied Colloids of Sufolk, N.J.), polymethacryloyloxyethyl trimethylammonium chloride (CTFA Polyquaternium 37)

The polymers were added to the formulations at levels of 0.1, 0.25, 0.37, 0.5 and 0.75% by weight according to the following table:

|  | Formula | | | | |
|---|---|---|---|---|---|
|  | 0.1 | 0.25 | 0.37 | 0.50 | 0.75 |
| Component | Formula Number Amount (grams) | | | | |
| Montanov 68 | 2.0 | 2.0 | 2.0 | 2.0 | 2.0 |
| Brij 76 | 0.5 | 0.5 | 0.5 | 0.5 | 0.5 |
| Polymer | 0.05 | 0.125 | 0.185 | 0.25 | 0.37 |
| Solvent 68:32 | 47.45 | 47.37 | 47.32 | 47.25 | 47.12 |

The formulations were prepared as in Example 1 except the polymers were added to the solvent (68:32 ethanol:water by weight) prior to mixing. Note that formula number refers to weight percent polymer. If the polymer was supplied in water, the water in the solvent system was corrected to reflect the exact formulation shown above. The results are shown below:

|  |  | Viscosity(cps) | | |
|---|---|---|---|---|
|  |  | Polymer added | Polymer added Post high shear | |
| Polymer | Concentration (weight %) | Before high shear | Initial time | 48 hours |
| None | 0 | 3700 | 3700 | — |
| Crodacel QS (1) | 0.1 | <500 | — | — |
|  | 0.25 | 22000 | — | — |
|  | 0.50 | 292000 | 178000 | 231000 |
|  | 0.75 | 152000 | 42500 | 93000 |
| Quatrisoft LM-200 (2) | 0.1 | <500 | — | — |
|  | 0.25 | 62000 | 32900 | 14700 |
|  | 0.37 | 31000 | — | — |
|  | 0.50 | <500 | — | — |
| Salcare (3) | 0.1 | 1550 | — | — |
|  | 0.25 | 1500 | — | — |
|  | 0.37 | 155000 | — | — |
|  | 0.50 | 296000 | — | — |

The results indicate that Crodacel QS with pendant stearyl groups has a synergistic effect on the viscosity of the composition. This is evident since the polymer itself contributes little thickening. Crodacel QS is supplied as a 20% aqueous solution and at concentrations under 1% by weight the viscosity of this polymer in 68:32 ethanol:water is less than 50 cps. It is believed that this polymer associates with the thickener system in the formulation. The Quatrisoft polymer also contributed to thickening the formulations. The Crodacel QS and Quatrisoft polymer formulations with the peak viscosity were prepared again except that the polymer was added to the thickener system after the composition was prepared and cooled to room temperature. Even under these conditions the polymer containing formulation had a higher viscosity than the formulation without the polymer. A preferred method of preparing the formulations is adding the polymer to the hot solvent before adding the thickener system so that the polymer and emulsifiers can interact while above the melt temperature. The Crodacel formulations were also found to be stable, showing no separation.

Example 6: Effect of Added Emollients

A series of wax, oil occlusive emollients and humectant type emollients were added to a thickener system to evaluate the effect on viscosity. Each emollient was added to two formulations shown below:

|  | Formula | |
|---|---|---|
|  | A | B |
| Component | Amount (grams) | |
| Montanov 68 | 4 | 1.8 |
| Brij 76 | 2 | 0.45 |
| Croadcel QS (20% solution in water) | 0 | 1.13 |
| Ethanol:water 68:32 by weight | 90.3 | 40 |
| Emollient | 3.7 | 1.7 |

The procedure of Example 1 was used to prepare the formulations except emollients were either added to the hot solvent or the thickener system prior to mixing. Glycerine and Quamectant were added to the solvent. Other emollients were added to the thickener system. The viscosity results are shown below:

|  |  | Viscosity(cps) | |
|---|---|---|---|
| Emollient Name | Chemical Description | A | B |
| Bernel Ester 2014[1] | octyldodecyl myristate | 12,900 | 39,000 |
| Bernel Citmol 320[1] | trioctyldodecyl citrate | 15,600 | 168,000 |
| Lipovol MOS 130[2] | tridecyl stearate and tridecyltrimellitate and dipentaerythritol hexacaprate | 28,000 | 39,000 |
| Fitoderm[3] | Squalane | 39,200 | 93,750 |
| DC344[4] | cyclomethicone | <100 | 2,700 |
| Jarcol I-16[5] | 2-hexyldecanol | <50* | 59,100 (0.5 wt %) 2,900 (1 wt %) |
| Lexol PG 865[6] | propyleneglycol dicaprylate/dicaprate | <50 | |
| Glycerin | glycerol | 28,600 | 274,000 |
| Quamectant AM50[7] | 6-(N-acetylamino)-4-oxahexyltrimethylammonium chloride | 61,000 | 141,000 |
| Astorwax OK 236[8] | paraffin wax |  | 39,000 |

[1]Bernel Chemical Co., Inc., Englewood, N.J.
[2]Lipo Chemical, Paterson, NJ.
[3]Hispano Quimica S.A. - Quimica Organica, Barcelona, Spain.
[4]Dow Corning, Midland, MI.
[5]Vista Chemical Co., Lisle, IL.
[6]Inolex Chemical Co., Philadelphia, PA
[7]Brooks Industries Inc., South Plainfield, NJ.
[8]AstorWax, Doravilla, GA.
*Formula A was completely solubilized. Therefore, this emollient was added to formula B at the reduced levels indicated.

This example shows that some emollients affect final viscosity of the composition. Humectants which are soluble in the system appear to have much less effect, such as glycerin. The greatest viscosity reduction appears due to adding emollients with branched chain hydrocarbons (e.g., Jarcol I-16).

Example 7: Effect of addition of Borate Ion

In this example sodium borate was added to a premade alkylpolyglucoside thickener composition. It is believed that the borate ion associates with adjacent polyglucose hydrophilic head groups to hold them in the "micelle" structure thus elevating the melt temperature.

A solution of sodium borate in water was added to a concentration of 0.7% by weight to the formulation of Example 6A containing Fitoderm squalane. The resulting formulation with sodium borate was visibly thicker with a higher melt temperature. The sample without borate melted rapidly when dispensed into the palm of a hand. The sample with borate did not melt when dispensed into the hand.

To evaluate the effect of borate ion at different pH values, 10.21 grams boric acid was added to 160 grams distilled water. Using a pH meter sodium borate was added while stirring until a pH of 5 was reached (0.33 grams sodium borate). A 57 gram sample was removed. To the remaining solution was added sodium borate to a pH of 6.0 (1.6 grams sodium borate). Again, a 57 gram sample was removed and to the remaining solution was added 1.94 grams sodium borate to reach a pH of 7.0. These three solutions were added to the following formulation:

| Component | Concentration (weight percent) |
| --- | --- |
| Montanov 68 | 4 |
| Brij 76 | 1 |
| Crodacel QS (20% solution in water) | 2.5 |
| Ethanol/water 68:32 | 92.5 |

The base formulation was prepared according to Example 1 with the Crodacel QS added to the solvent system prior to mixing. The borate solutions were added to yield the weight percent borate shown in the table below after the thickener system had cooled to room temperature. The following observations and melt temperatures were recorded:

| Borate Soln pH | wt % Boron | Consistency | Tm (° C.) |
| --- | --- | --- | --- |
| None- CONTROL | 0 | Stable | <31 |
| 5 | 0.02 | stable and thicker than control | 31 |
| 5 | 0.04 | thicker than pH 5 with 0.02% Borate | 34 |
| 5 | 0.08 | thicker than pH 5 with 0.04 Borate | 35.5 |
| 5 | 0.12 | similar to pH 5 with 0.08 Borate | >35.5, <39 |
| 6 | 0.02 | syneresis, not as thick as pH 5 analog | <31 |
| 6 | 0.04 | syneresis, not as thick as pH 5 analog | 31–34 |
| 6 | 0.08 | syneresis, not as thick as pH 5 analog | 31–34 |
| 6 | 0.11 | syneresis, not as thick as pH 5 analog | 35.5 |
| 7 | 0.014 | more phase separation than pH 6 analog, no thickening | <31 |
| 7 | 0.04 | more phase separation than pH 6 analog, no thickening | <31 |
| 7 | 0.07 | more phase separation than pH 6 analog, no thickening | 31 |
| 7 | 0.10 | more phase separation than pH 6 analog, no thickening | 31 |

The results show that adding borate ion to the composition increases the melt temperature. This is more pronounced at lower pH values.

Example 8: Effect of Ethanol Concentration on Melt Temperature:

Formulations containing 7% Montanov 68, 1.76% Brij 76, 0.5% Crodacel QS polymer (on a solids basis) were prepared in accordance with Example 5. For each formulation the percent solvent was held constant at 90.74% but the ratio of ethanol:water was varied from 50:50 to 68:32. The melt temperature was measured as described above.

| Solvent ratio Ethanol:water | Melt Temp (° C.) |
| --- | --- |
| 50:50 | 40 |
| 55:45 | 38.5 |
| 60:40 | 36 |
| 64:36 | 36 |
| 68:32 | 33 |

The results illustrate that as the alcohol:water ratio is increased, the melt temperature decreases for this thickener system.

Example 9: Antimicrobial Efficacy of Compositions Containing Chlorhexidine Gluconate The following thickener systems were produced with and without chlorhexidine gluconate (CHG) to determine if the CHG is effectively delivered in a thickener system. The borate pH 5 solution from Example 7 was used.

| | Formula Amount (grams) | | | | | | | | | |
| --- | --- | --- | --- | --- | --- | --- | --- | --- | --- | --- |
| Component | 1 | 2 | 3 | 4 | 5 | 6 | 7 | 8 | 9 | 10 |
| Montanov 68 | | | 2.0 | 0.77 | 2 | 0.76 | 2 | 0.76 | 2.0 | 0.69 |
| Brij 76 | | | 0.5 | 0.19 | 0.5 | 0.19 | 0.5 | 0.19 | 0.5 | 0.17 |
| Crodacel QS (20%) | | | | | 1.25 | 0.48 | 1.25 | 0.48 | 1.25 | 0.43 |
| Kenamide B (behenamide, Witco) | | | | | | | 0.25 | 0.10 | | |
| Borate ion solution, pH 5 | | | | | | | | | 5.61 | 1.93 |
| CHG (20% soln) | | 0.25 | | 0.48 | | 0.48 | | 0.48 | | |
| Ethanol:water 68:32 | | | 47.5 | 18.2 | 46.25 | 17.6 | 46 | 17.5 | 46.25 | 15.9 |
| Ethanol | 6.8 | 6.77 | | | | | | | | |
| Water | 3.2 | 2.98 | | | | | | | | |

The Minimum Inhibitory Concentration (MIC) for both *E. Coli* and *S. Aureus* was determined according to the test methods outlined above and is reported in the table below:

|  | MIC ($\mu$g/ml) | |
| --- | --- | --- |
| Sample | E. coli | S. aureus |
| 1 | >256 | >256 $\mu$g/ml |
| 2 | 4–8 | 4 |
| 3 | >256 | >256 |
| 4 | 2–4 | 2 |
| 5 | >256 | >256 |
| 6 | 4 | 4 |
| 7 | >256 | >256 |
| 8 | 4 | 4 |
| 9 | >256 | >256 |
| 10 | 4–8 | 4 |
| 0.5% CHG std. | 4 | 4 |
| Hibiclens* | 4 | 4 |

*4% w/v CHG antimicrobial soap sold by Stuart Pharmaceuticals

The results show that none of the components of this formulation of the invention inactivate the CHG.

Example 11: A Presurgical Antimicrobial Hand Lotion Using an Alkylpolyglucoside Containing Thickener System The following formulation was prepared using the procedure of Example 6:

| Component | Wt. % |
| --- | --- |
| Montanov 68 | 4.0 |
| Brij 76 | 1.0 |
| Kenamide B | 0.5 |
| Lipovol MOS 130 | 1.5 |
| Fitoderm | 2.3 |
| 350 ctk polydimethyl siloxane (Carbide L45/350) | 0.50 |
| Crodacel QS (20% solution in water) | 2.5 |
| NaCl (2% in water)* | 2.5 |
| Ethanol | 59.3 |
| Water | 25.9 |

*Sodium chloride was added at a level of 0.05% to mimic the ionic strength of 0.5% CHG.

The resulting formulation had an ethanol:water ratio of 68:32. This formulation was applied to hands repeatedly throughout the day by several volunteers. Hands were washed with Ivory soap between applications. The feel of the lotion was well received and skin condition was maintained.

Example 12: Alkylpolyglucoside/Polyethoxylated alkyl alcohol/Ester of Short Chain Alcohol/Amine Oxide/Quaternary Amine Thickener Systems The following compositions were prepared by heating separately the solvent (alcohol and water) and the thickener system to 70° C. The solvent was rapidly added to the thickener system and homogenized on a Silverson L4R homogenizer. This was followed by 10 minutes of stirring with an overhead inverted "T" paddle stirrer with the glass container immersed in a 10–15° C. water bath. Compositions A–C were mixed for 10 minutes while C and D were mixed for 4 and 5 minutes respectively. The compositions were then cooled to allow the emulsifiers to solidify.

| Component | A | B | C | D | E | F | G |
| --- | --- | --- | --- | --- | --- | --- | --- |
|  | Amount (grams) | | | | | | |
| Montanov 68 | 1.2 | 1.2 | 1.2 | 3.2 | 3.2 | 1.80 | 1.80 |
| Brij 76 | 0.3 | 0.3 | 0.3 | 0.8 | 0.8 | 0.45 | 0.45 |
| Incromine oxide B30P*(30% solution in water) | 0.5 | 0.75 | 1.0 | | | | |
| Nikkol CA-2580** | | | | 0.18 | 0.35 | | |
| Incroquat DMB-90****(90% in 10% ethanol) | | | | | | 0.50 | 0.50 |
| Lanette 22 | | | | 0.65 | 1.3 | | |
| Kemester 9022*** | 0.6 | 0.6 | 0.6 | 1.6 | 1.6 | | 0.23 |
| 68:32 Ethanol/water | 27.40 | 27.15 | 26.90 | 73.57 | 72.57 | 40.45 | 40.23 |

*Incromine oxide B-30P = behenamine oxide available from Croda Inc., Parsippany, NJ
**Nikkol CA-2580 = Behenyltrimethylammonium Chloride, Barnet Products Corp., Paterson, NJ
***Kemester 9022 = methyl behenate, Witco, Humko Chemical Div. Memphis TN
****Incroquat DBM-90 = Dibehenyldimethylammonium methosulfate available from Croda Inc., Parsippany, NJ Compositions A, B, and C were viscous creams with little elasticity. Visually, sample C was more viscous than B which was more viscous than A. This shows that the amine oxide contributed to the viscosity of the compositions. Compositions D and E were very viscous and quite elastic in nature. Composition E was significantly thicker. This shows that this quaternary amine contributed to a more elastic composition. Samples F and G were opaque white creams of good consistency. Sample G was more viscous than Sample F. Sample F had some syneresis.

The melting temperature (Tm) of the compositions was measured according to the protocol outlined above. The results are shown below:

| Composition | A | B | C | D | E | F | G |
| --- | --- | --- | --- | --- | --- | --- | --- |
| Tm (° C.) | 37–39 | 39 | 39 | 39 | 42 | 38 | 38 |
| Heat cycle * | HS | HS | HS | HS | HS | HS | HS |

* Once the samples were melted, they were allowed to very slowly cool to room temperature by simply turning off the water bath. The time to cool was several hours. The samples were judged as heat stable (HS) if macroscopically they appeared the same as the original sample.

Example 13: Long Chain Alkylpolyglucoside/Poyethoxylated alkyl alcohol/Quaternary Amine Thickener System A series of 10 formulations were prepared using a three component mixture design with the total emulsifier level fixed at 2% by weight. The following concentration ranges were investigated using a solvent ratio of 68:32 ethanol:water further containing 0.5% by weight CHG.

| Emulsifier | Percent by weight |
| --- | --- |
| Eassi 624MP | 0.25–1.5% by weight |
| Nikkol BB5 | 0.25–1.5 |
| Incroquat DBM-90 | 0.25–1.5 |

Eassi 624MP is an alkylpolyglucoside prepared from an alcohol feed stock of 92% by weight behenyl alcohol and was obtained from Seppic Inc., Fairfield, N.J. The product had a melting point of 83° C. and a 5% aqueous solution had a pH of 6.4. Each formulation was prepared by adding 49 grams solvent at 80° C. to 2 grams thickener system at 80° C. followed by 45 seconds of homogenization followed by 3 minutes of overhead mixing while immersed in a 15° C. water bath. The samples were subsequently diluted to 2% solids by adding 49 grams solvent mixture. Each composition was subsequently tested for viscosity and Tm. The viscosities of the resulting formulations ranged from less than 165,000 cps to 309,000 cps. Examples of several preferred formulations appear below:

| Component | Sample | | | | | |
|---|---|---|---|---|---|---|
| | A | B | C | D | E | F |
| | Amount (grams) | | | | | |
| Eassi 624MP | 1.5 | 1.08 | 0.25 | 0.66 | 0.25 | 0.87 |
| Nikkol BB5 | 0.25 | 0.46 | 1.5 | 0.67 | 0.88 | 0.88 |
| Incroquat DBM 90 (90%) | 0.25 | 0.46 | 0.25 | 0.66 | 0.87 | 0.25 |
| Viscosity (cps) | 309,000 | 192,000 | 175,000 | 227,000 | 252,000 | 220,000 |
| Tm (° C.) | >57° C. | 52–57 | 52 | 52–57 | 44 | 52–57 |

The results show that the behenylpolyglucoside increases the melt temperature. Comparing the melt temperatures of this example with those of Example 12F shows that increasing the chain length of the hydrophobes in the thickener system increases the Tm. The thickener system of the formulations in this example produce homogenous viscous creams with varying ratios of the emulsifiers.

Example 14: Disinfectant Hand Lotion based on Alkylpolyglucoside/Polyethoxylated alkyl alcohol/Quaternary Amine Thickener System Disinfectant hand creams/lotions were prepared based on the thickener system of Example 13F. The compositions are shown below:

| Component | A | B |
|---|---|---|
| | Amount (grams) | |
| Eassi 624MP | 0.88 | 0.88 |
| Nikkol BB5 | 0.87 | 0.87 |
| Incroquat DBM 90 (90% solution in ethanol) | 0.25 | 0.25 |
| Silwet 7001* (75% solution in water) | 1.33 | 1.33 |
| DC344[1] | 2.00 | 2.00 |
| Procetyl 50** | 2.0 | |
| Macol 30P''' | | 1.00 |
| Arcol PPG-725*** | 2.00 | 2.00 |
| Bernel Ester 2014 | | 2.00 |
| Pluronic P-65**** | | 0.50 |
| 68:32 ethanol:water | 91 | 89 |

*Silwet 7001 = a methyl terminated polyether pendant silicone copolyol having a polyethylene oxide/polypropylene oxide ratio of 40/60 and a molecular weight of 20,000 available from OSI Specialties Inc.
**Procetyl 50 = PPG-50 cetyl ether, Croda Inc.
***Arcol PPG-725 = polypropylene glycol having a molecular weight of approximately 750, Arco Chemical Co.
****Pluronic P-65 = polyethylene oxide capped polypropylene oxide having a EO/PO mole ratio of 1 and a molecular weight of approximately 3400 available from BASF Wyandotte Corp. Parsippany, NJ.
'''Macol 30P = PPG-30 cetyl ether, PPG Industries Inc., Mazer Chemical, Gurnee, Ill.
[1]DC344 = D4, D5, cyclodimethicone available from Dow Corning, Midland, MI.

The compositions were prepared by heating the solvent and Silwet to 75° C. in one container and heating the remaining components to 75° C. in a second container. The solvent was rapidly added to the emulsifiers/emollients followed by 45 seconds of homogenization with no subsequent mixing. Both formulae had a nice feel when 2 ml was applied to the hands and rubbed in the skin. Formula B was a little more appealing due to a better hand feel. Tm was measured as 48° C. for A and 45.5° C. for B.

Example 15: Polyglycerol Ester Containing Thickener Systems

The formulations for Example 15 (as described in the table below) were prepared by heating the thickener system and the solvent in separate jars to 75° C., rapidly adding the solvent to the thickeners, shaking vigorously, and stirring with an overhead stirrer for 10 minutes while immersed in a 10–15° C. water bath. The Tm was measured as described above.

| Component | Chemical Description | Sample | | |
|---|---|---|---|---|
| | | A | B | C |
| | | Amount (grams) | | |
| Decaglyn 1-S | decaglycerolmonostearate, Barnet of Paterson, NJ | 1.35 | | |
| Hexaglyn 1-S | hexaglycerolmonostearate, Barnet of Paterson, NJ | | 1.35 | |
| Tetraglyn 1-S | tetraglycerolmonostearate, Barnet of Paterson, NJ | | | 1.35 |
| Brij 76 | Steareth-10 | 0.23 | 0.23 | 0.23 |
| Ethanol:water 68:32 | | 42.98 | 42.98 | 42.98 |
| Tm (° C.) | | 44 | 38.5 | 38.5 |

The samples were tested for stability. Samples A, B and C produced stable compositions of varying viscosity. Visual observation showed that sample A had a higher viscosity than B which was higher than C. A longer polyglycerol chain length is preferred in this thickener system and even though the longer chain polyglycerol emulsifier is expected to be more soluble in the solvent system, it increased the Tm of the formulation.

Example 16: More Polyglycerol Ester Containing Thickener Systems

The following compositions were prepared as described in Example 15.

| Component | Sample | |
|---|---|---|
| | A | B |
| | Amount (grams) | |
| Decaglyn 1-S Polyaldo 10-1-S* | 1.5 | 1.5 |
| Brij 76 | 0.5 | 0.5 |
| Incroquat DBM90 | 0.56 | 0.38 |
| Arcol PPG-425*** | | 2.0 |
| Procetyl 50 | | 2.0 |
| Ethanol/water 68:32 | 47.44 | 43.63 |
| Tm (° C.) | 39–41 | 40–44 |

*Polyaldo 10-1-S = decaglycerolmonstearate, Lonza of Fairlawn, NJ.
**Promyristyl PM-3 = PPG-3 myristyl ether, Croda of Parsippany, NJ.
***Arcol PPG-425 = polypropylene glycol, MW = approximately 450, Arcol Chemical Co.

Samples A and B were homogenous viscous translucent almost gel-like compositions. Sample B had a fairly nice feel but was a little tacky.

Example 17: Polyglycerol ester/Amine Oxide/Quaternary Amine Thickener Systems The following compositions were prepared as described in Example 15. The viscosity (Tm) was measured for each sample.

|  | Sample | | | |
|---|---|---|---|---|
| Component | A | B | C | D |
|  | Amount (grams) | | | |
| Polyaldo 10-1-S | 1.2 | 0.9 | 0.6 | 0.3 |
| Incromine Oxide B30P (30% solution in water) | 1.0 | 2.0 | 3.0 | 4.0 |
| Incroquat DBM-90 (90% soltion in ethanol) | 0.28 | 0.28 | 0.28 | 0.28 |
| Ethanol:water 68:32 | 47.5 | 46.8 | 46.1 | 45.4 |
| Viscosity (cps) | 530,000 | 105,000 | 146,000 | 75,000 |
| Tm (° C.) | 40 | 40 | 40 | 37 |

The samples were allowed to cool after melting. All samples produced translucent gel-like compositions of acceptable viscosity and melt temperature. Samples C and D returned to a uniform appearance after heating above the melt temperature and allowing to slowly cool.

Example 18: Decaglyceroltetrabehenate Containing Thickener System

The following compositions were prepared by heating the thickener system and solvent in separate jars to 80° C., rapidly adding the solvent to the thickener, homogenizing for 20 seconds, and stirring with an overhead stirrer for 10 minutes while immersed in a 10–15° C. water bath. The Tm and viscosity were measured for some of the samples.

|  | Sample | | | | | | | |
|---|---|---|---|---|---|---|---|---|
| Component | A | B | C | D | E | F | G | H |
|  | Amount (grams) | | | | | | | |
| Kemester 9022 | 0.8 | 0.60 | 0.40 | 0.20 |  |  |  |  |
| Incromine Oxide B30P (30% solution in water) |  |  |  |  | 2.67 | 2.0 | 1.33 | 0.67 |
| Decaglyceroltetrabehenate | 0.20 | 0.40 | 0.60 | 0.80 | 0.20 | 0.40 | 0.60 | 0.80 |
| Ethanol:water 68:32 | 48.72 | 48.72 | 48.72 | 48.72 | 46.86 | 47.32 | 47.79 | 48.26 |
| Tm (° C.) | 49 | — | — | — | — | 39 | 39 | — |
| Viscosity (cps) | 135,000 | — | — | — | 8,500 | 6,500 | 6,700 | 10,500 |

Samples B–D produced homogenous compositions of low viscosity. Sample A was an opaque viscous cream with a fairly high melt temperature. Samples E–H were lower in viscosity and melt temperature than Sample A.

Example 19: Ester/Amine Oxide/ Quaternary Amine Thickener Systems

The following compositions were prepared using the procedure outlined in Example 15.

|  | Sample | | | |
|---|---|---|---|---|
| Component | A | B | C | D |
|  | Amount (grams) | | | |
| Kemester 9022 | 0.9 | 0.9 | 0.9 | 0.9 |
| Incromine Oxide B30P (30% solution in water) | 2.0 | 2.0 | 2.0 | 2.0 |
| Nikkol CA-2580 (85% solution in water) | 0.29 | 0.17 |  |  |
| Incromine BB gluconate (36.5% solution in water) |  |  | 0.68 | 1.37 |
| Ethanol:water 68:32 | 46.81 | 46.93 |  |  |
| Ethanol |  |  | 31.42 | 30.82 |
| water |  |  | 15.0 | 14.91 |
| Tm (° C.) | — | — | 49 | — |

Samples A and B did not produce stable homogenous compositions. Composition C and D produced viscous compositions but composition D appeared non-uniform. The melt temperature of Composition C was quite high.

Example 20: Amine Oxide/Ester/ Quaternary Amine Thickener System

A series of 18 formulations were prepared using a three component mixture design. The total thickener level varied from 2.45 to 4.55% by weight. The following concentration ranges were investigated using a solvent ratio of 68:32 ethanol:water.

| Component | Percent by weight |
|---|---|
| Incromine Oxide B30P | 0.80–1.87 |
| Kemester 9022 | 1.40–2.47 |
| Incroquat DBM-90 | 0.05–0.92 |

The compositions were prepared by heating the thickener system and the solvent in separate jars to 75° C., rapidly adding the solvent to the emulsifiers, shaking vigorously, and stirring with an overhead stirrer for 5 minutes while immersed in a 10–1 5° C. water bath. The melt temperature (Tm), viscosity and stability were measured as described above. All ratios produced stable compositions having a viscosity range of 10,000–270,000 cps and a Tm of 45–47° C. Elasticity was measured by gently stirring the sample and was judged on a scale of 1–5 where 5 was a very stringy composition and 1 was viscous but not elastic. A few of the compositions prepared are shown below:

|  | Composition | | | | |
|---|---|---|---|---|---|
| Component | A | B | C | D | E |
|  | Amount (grams) | | | | |
| Kemester 9022 | 1.17 | 1.43 | 1.17 | 1.17 | 1.17 |
| Incromine Oxide B30P (30% solution in water) | 2.6 | 3.47 | 4.06 | 1.14 | 2.60 |
| Incroquat DBM90 (90% solution in ethanol) | 0.60 | 0.33 | 0.30 | 0.33 | 0.05 |
| Ethanol:water 68:32 | 60.63 | 59.45 | 59.45 | 62.36 | 61.18 |
| Tm (° C.) | 47 | 45 | 45 | 46 | 45 |

-continued

|  | Composition | | | | |
|---|---|---|---|---|---|
| Component | A | B | C | D | E |
| Viscosity (cps) | 280,000 | 270,000 | 270,000 | 250,000 | 30,000 |
| Elasticity (1–5) | 2 | 4.5 | 4 | 1 | 5 |

The results indicate that this thickener system produces stable compositions with varying ratios of emulsifiers but that the physical properties of the compositions vary widely. Composition D is a preferred formulation since it is high in viscosity at low total solids content (2.83%), has very little elasticity and a high melt temperature.

The following disinfectant hand lotion was produced using the thickener system and the procedure of Example 14:

| Component | Amount (grams) |
|---|---|
| Kemester 9022 | 0.72 |
| Incromine Oxide B30P (30% solution in water) | 1.48 |
| Incroquat DBM90 (90% solution in ethanol) | 0.10 |
| Pluronic P65 | 0.25 |
| Bernel Ester 2014 | 1.00 |
| Macol CA30P | 0.50 |
| PPG725 | 1.00 |
| DC344 | 1.10 |
| Silwet 7001 | 0.70 |
| 68:32 ethanol:water | 43.28 |

This composition was stable with a nice viscosity and a Tm of 41° C.

Example 21: Alkyl Alcohol/Quaternary Amine Thickener System

The following formulations were prepared using Lanette 22 (Henkel Corp of Ambler, Pa.), Behenyl Alcohol Nikkol CA-2580 (Barnet Products Corp., Paterson, N.J.), Behenyltrimethylammonium Chloride.

|  | Composition | | |
|---|---|---|---|
| Component | A | B | C |
|  | Amount (grams) | | |
| Nikkol CA-2580 | 0.59 | 0.59 | 0.44 |
| Lanette 22 | 1.5 | 2.00 | 1.63 |
| 68:32 Ethanol:water | 47.91 | 47.41 | 47.93 |

The compositions were prepared by separately heating the solvent and the thickener system to 65–70° C. The solvent was rapidly added to the thickener system followed by stirring with an overhead paddle stirrer with the glass container immersed in a 10° C. water bath. Each composition was mixed for 4.5 minutes after which the compositions cooled sufficiently for the emulsifiers to solidify.

All three compositions were viscoelastic. The samples appeared pearlescent with macroscopically obvious crystalline regions. The crystals appeared macroscopically lamellar in nature. A small amount of syneresis was seen on standing at 23° C. overnight. The Tm of sample C was approximately 47° C. (The sample did not melt uniformly and even at 47° C. still had some solid regions.)

Example 22: Alkyl Alcohol/Ester/Quaternary Amine Thickener Systems

A series of 10 formulations were prepared using a three component mixture design. The total thickener system level was held constant at 2.00% by weight. The following concentration ranges were investigated using a solvent ratio of 68:32 ethanol:water containing 0.5% by weight CHG:

| Component | Percent by weight |
|---|---|
| Lanette 22 | 0.25–1.25 |
| Kemester 9022 | 0.50–1.50 |
| Incroquat DBM-90 | 0.25–1.25 |

The compositions were prepared by heating the thickener system and the solvent in separate jars to 75° C., rapidly adding the solvent to the thickener, homogenizing for 40 seconds on a Silverson L4R homogenizer at maximum speed, and stirring with an overhead stirrer for 5 minutes while immersed in a 10–15° C. water bath. The Tm, viscosity and stability were measured. Only select ratios produced high viscosity stable compositions having a viscosity range of 76,000–274,000 cps and a Tm of 47–53° C. Stability was measured according to Example 1. Several of the formulations are shown below:

|  | Sample | | | | |
|---|---|---|---|---|---|
| Component | A | B | C | D | E |
|  | Percent by weight | | | | |
| Kemester 9022 | 1.50 | 0.50 | 1.00 | 0.50 | 0.67 |
| Lanette 22 | 0.25 | 0.25 | 0.75 | 1.25 | 0.92 |
| Incroquat DBM90 | 0.25 | 1.25 | 0.25 | 0.25 | 0.42 |
| Ethanol:water 68:32 (0.5% CHG) | 98 | 98 | 98 | 98 | 98 |
| Tm (° C.) | 47 | 49 | 51 | 52 | 53 |
| Viscosity (cps) | 76000 | 76000 | 250000 | 274000 | 125000 |
| Stability (% Volume separation) | <2 | 2 | 2 | 10 | 5 |

The results indicate that this thickener system produces stable compositions with varying ratios of emulsifiers but that the physical properties of the compositions differ considerably. Composition C is a particularly preferred formulation since it has a high viscosity, high melt temperature, and little separation. After standing for 1–2 days at 23° C., all of the above formulae showed a small amount of syneresis, i.e. a small amount of clear low viscosity solvent phase separated on the top of the sample.

Example 23: Addition of an Alkylene Alcohol

Oleyl alcohol was incorporated into the formulation shown in Example 22C by adding it to the molten thickeners prior to mixing with the solvent. The composition is shown below:

| Component: | Amount (grams) |
|---|---|
| Lanette 22 | 0.38 |
| Kemester 9022 | 0.50 |
| Incroquat DBM90 | 0.14 |
| Novol (oleyl alcohol, Croda) | 0.20 |
| Ethanol:water 68:32 | 48.78 |

A stable quite viscous gel-like composition resulted. The Tm was measured as 50° C. The stability was measured as 5%.

Example 24: Addition of Dialkoxy Dimethicone and Polyether-Polysiloxane Copolymers for Enhanced Stability The compositions of Example 22 had very good viscosity, Tm, and stability properties but showed a slight amount of syneresis on standing. Surprisingly, adding a combination of dialkoxy dimethicone and polyether-polysiloxane copolymers ensured no syneresis and also provided a smooth non-waxy feel. The following system was prepared using the thickener ratios identified in Example 22C and the procedure of Example 22. The Abil wax2440 was heated with the emulsifiers while the Abil B88183 was heated in the solvent:

| Base Systems | |
|---|---|
| Component | Amount (grams) |
| Kemester 9022 | 0.50 |
| Lanette 22 | 0.38 |
| Incroquat DBM90 (90% solution in ethanol) | 0.14 |
| Abil wax2440[1] | 0.25 |
| Abil B88183[2] (35% solution in water) | 0.71 |
| Ethanol:water 72:28 | 48.03 |
| Tm (° C.) | 47 |

[1]Abil wax2440 = dibehenoxypolydiemthyl siloxane available from Goldschmidt Chemical Corp., Hopewell, VA.
[2]Abil B88183 = dimethicone copolyol having a EO/PO ratio of 77/23 and a viscosity in water at 35% solids at 25 C. of 95mm$^2$/sec available from Goldschmidt Chemical Corp., Hopewell, VA.

The system was stable and showed no signs of syneresis even after 13 days of room temperature storage. The melt temperature of the base formulation is reduced compared to that of Example 22C most likely due to the increase in the level of ethanol in the solvent.

This formulation was evaluated for activity of CHG at 0.5% by weight and was also used to prepare a hand lotion containing numerous emollients by preparing the following formulations:

| Component | Weight % |
|---|---|
| Kemester 9022 | 1.0 |
| Lanette 22 | 0.75 |
| Incroquat DBM90 (90% solution in ethanol) | 0.28 |
| Abil 2440 | 0.75 |
| Abil 88183 (35% solution in water) | 1.43 |
| glycerin | 2.50 |
| Dermol DIPS | 1.00 |
| Dermol 489[2] | 1.00 |
| Arcol PPG 725 | 2.00 |
| DC344 | 0.50 |
| Dermol G-7DI[1] | 0.5 |
| Ethanol:water 68:32 | 88.29 |

[1]Dermol G-7DI = glycereth-7-diisononanoate available from Alzo Inc. Sayerville, NJ
[2]Dermol 489 = diethyleneglycol dioctanoate/diisononanoate available from Alzo Inc. Sayerville, NJ The formulation was first evaluated in tactile testing by applying 2 ml in the palm of one hand and rubbing the lotion thoroughly into both hands. This composition had good cosmetic properties. A panel of five volunteers then applied the lotion as described eight times a day in approximately 1 hour intervals after first washing with water and Ivory liquid soap (Procter and Gamble, Cincinnati, Ohio) and drying the hands thoroughly before each application. This was repeated for a total of 5 days and was conducted during the winter to exaggerate any potential drying effect. The lotion was rated positively in all cosmetic categories surveyed including overall feel, lack of oiliness, moisturization, smoothness during application, and feel while washing. Expert grading was used to judge the condition of the skin. Using a 5 point scale: 1=Very slightly scaly—occasional scale not necessar-

| | Sample | | | | | | | |
|---|---|---|---|---|---|---|---|---|
| Component | 1 | 2 | 3 | 4 | 5 | 6 | 7 | 8 |
| | Amount (grams) | | | | | | | |
| Kemester 9022 | | | 1.00 | 0.52 | 1.00 | 0.50 | 1.00 | 0.51 |
| Lanette 22 | | | 0.75 | 0.39 | 0.75 | 0.38 | 0.75 | 0.38 |
| Incroquat DBM90 (90% solution in ethanol) | | | 0.28 | 0.15 | 0.28 | 0.14 | 0.28 | 0.14 |
| Abil 2440 | | | | | 0.75 | 0.38 | 0.75 | 0.38 |
| Abil 88183 (35% solution in water) | | | | | 1.43 | 0.72 | 1.43 | 0.72 |
| Pluronic P65 | | | | | | | 0.50 | 0.26 |
| glycerin | | | | | | | 1.00 | 0.51 |
| Dermol DIPS[1] | | | | | | | 1.00 | 0.51 |
| Macol CA30P | | | | | | | 1.00 | 0.51 |
| Arcol PPG 725 | | | | | | | 2.00 | 1.03 |
| DC344 | | | | | | | 2.00 | 1.03 |
| CHG soln (20% in water) | | 0.25 | | 1.39 | | 1.26 | | 1.28 |
| Ethanol:water 68:32 | | | 97.97 | 51.21 | 95.79 | 48.15 | 88.29 | 45.29 |
| Ethanol | 6.8 | 6.77 | | | | | | |
| Water | 3.2 | 2.98 | | | | | | |
| E. coli 223 MIC (μg/ml) | >256 | 4 | >256 | 24 | >256 | 2–4 | >256 | 4 |
| S aureus 502 MIC (μg/ml | >256 | 4 | >256 | 2 | >256 | 4 | >256 | 4 |

[1]Dermol DIPS = diisopropyl sebacate available from Alzo Inc. Sayerville, NJ

A 0.5% CHG standard was also run and found to have an MIC of 4 for both bacterial strains. These results indicate that the thickener system does not interfere with the CHG activity and that the compositions have no inherent antimicrobial activity except due to the ethanol:water solvent system. Sample 7 had nice cosmetic properties.

Example 25: Repeat Application of a Preferred Hand Lotion Composition

The following hand lotion composition was prepared as described in Example 23.

ily uniformly distributed 2=Slightly Scaly—Scale in sulci and on plateaus. More visible scale that is more uniformly distributed 3=Scaly—Visible scale giving the overall appearance of the skin surface a whitish appearance. Definite uplifting of edges or scale-sections. Hand is rough to the touch. 4=Scaly to very scaly—More scale and pronounced separation of scale edges from skin, although they may still be lying flat on the skin surface. Some evidence of cracking in sulci and on plateaus. Some reddening may appear.

5=Very scaly—excessive cracking of skin surface. Skin appears very irritated with widespread reddening The skin condition was evaluated initially and at the end of days 3 and 5 and results are shown in the table below.

| Time | Mean Skin Rating* | Standard Deviation |
|---|---|---|
| Initial | 2.6 | 0.93 |
| Day 3 | 1.80 | 1.53 |
| Day 5 | 1.60 | 0.77 |

*five subjects two hands each (n = 10)

The results indicate that overall the skin condition significantly improved.

Example 26: Polyethoxylated Alcohol/Ester/ Quaternary Amine Thickener System The following thickener system compositions were prepared by heating the solvent and the thickener system separately to 75° C. The solvent was added to the thickener system and homogenized on a Silverson L4R at maximum speed for 45 seconds followed by stirring with an overhead paddle stirrer in a glass container immersed in a 20° C. water bath. Each composition was mixed for 3 minutes and the compositions were cooled sufficiently to allow the thickeners to solidify.

| | Composition | | | |
|---|---|---|---|---|
| Component | A | B | C | D |
| | Amount (grams) | | | |
| Unithox 450[1] | 0.18 | 0.35 | 0.53 | 0.70 |
| Kemester 9022 | 0.70 | 0.53 | 0.35 | 0.18 |
| Incroquat DBM-90(90% solution in ethanol) | 0.13 | 0.13 | 0.13 | 0.13 |
| Ethanol:water 70:30 | 49.00 | 49.00 | 49.00 | 49.00 |
| Tm (° C.) | 47 | 47–50 | 47–50 | 42 |

[1]Unithox 450 is a polyethoxylated alkyl alcohol having an alkyl chain length of approximately 36 carbons and nine units of ethylene oxide having a molecular weight of 2125 available from Petrolite Specialty Polymers Group, Tulsa, OK.

All four formulations formed viscous compositions. Formula B was more translucent and gel-like than A. Formulation D appeared less viscous. The melt temperatures were higher at ratios of Unithox 450:Kemester 9022 of 0.66 to 1.5 but were fairly high for all formulations.

Example 27: Polyethoxylated Alcohol/Ester/ Quaternary Amine Thickener System The following thickener systems were prepared according to the procedure of Example 26:

| | Composition | | | |
|---|---|---|---|---|
| Component | A | B | C | D |
| | Amount (grams) | | | |
| Abil 2440 | 0.18 | 0.35 | 0.53 | 0.70 |
| Kemester 9022 | 0.70 | 0.53 | 0.34 | 0.18 |
| Incroquat DBM-90 | 0.13 | 0.13 | 0.13 | 0.13 |
| Ethanol:water 68:32 | 49.00 | 49.00 | 49.00 | 49.00 |

Formulation A produced a stable thick creamy composition having a Tm of 44–45° C. Formulations B and C were quite low in viscosity and Formulation D showed almost no increase in viscosity.

Example 28: Alkylene Alcohol/Ester/Quaternary Amine Thickener System

The following thickener systems were prepared according to the procedure of Example 26 except that the composition was homogenized for only 15 seconds.

| | Formulation | | | |
|---|---|---|---|---|
| Component | A | B | C | D |
| | Amount (grams) | | | |
| Novol | 1.08 | 0.81 | 0.54 | 0.27 |
| Kemester 9022 | 0.27 | 0.54 | 0.81 | 1.08 |
| Incroquat DBM-90 | 0.25 | 0.25 | 0.25 | 0.25 |
| Ethanol:water 60:40 | 43.40 | 43.40 | 43.40 | 43.40 |
| Viscosity (cps) | unstable | low | 125,000 | 340,000 |

Formulation A was unstable and showed significant phase separation. Formulation B was homogenous and had very low viscosity. Formulation C was a viscous cream but showed some syneresis on standing. Formulation D was opaque and gel-like with a high viscosity and showed only a slight amount of syneresis.

Example 29: Alkylene Alcohol/Ester/Amine Oxide Thickener System

The following thickener systems were prepared according to the procedure of Example 28.

| | Formulation | | | |
|---|---|---|---|---|
| Component | A | B | C | D |
| | Amount (grams) | | | |
| Novol | 1.08 | 0.81 | 0.54 | 0.27 |
| Kemester 9022 | 0.27 | 0.54 | 0.81 | 1.08 |
| Incromine Oxide B30P | 1.80 | 1.80 | 1.80 | 1.80 |
| Ethanol:water 60:40 | 41.85 | 41.85 | 41.85 | 41.85 |
| Viscosity (cps) | 1,750 | 15,700 | 40,800 | 65,400 |

Composition A was translucent, fairly elastic and low in viscosity. Composition B was translucent, pearlescent, and fairly elastic but significantly more viscous then composition A. Compositions C and D were pearlescent, slightly opaque, and fairly elastic with higher viscosities.

Example 30: Alkyl Phospholipid/Polyethoxylated Alkyl Alcohol Thickener System The following thickener systems were prepared according to the procedure of Example 28.

| Component | Formulation | | | | | | | |
|---|---|---|---|---|---|---|---|---|
| | A | B | C | D | E | F | G | H |
| | Amount (grams) | | | | | | | |
| Phospholipid SV[1] (35% solution in water) | 1.08 | 0.81 | 0.54 | 0.27 | | | | |
| Behenylphospholipid[2] (40% solution in water) | | | | | 2.7 | 2.03 | 1.35 | 0.68 |
| Nikkol BB-5 | 0.27 | 0.54 | 0.81 | 1.08 | 0.27 | 0.54 | 0.81 | 1.08 |
| Ethanol:water 60:40 | 43.65 | 43.65 | 43.65 | 43.65 | | | | |
| Ethanol | | | | | 25.72 | 25.84 | 25.96 | 26.07 |
| Water | | | | | 16.31 | 16.60 | 16.88 | 17.17 |
| Viscosity (cps) | <100 | <100 | 6,170 | 4,590 | <100 | <100 | 6,300 | 29,400 |
| Viscosity (cps) post CHG Addition | | | 9,000 | 12,400 | | | 6,400 | 37,200 |

[1]Phospholipid SV is a zwitterionic surfactant that is stearamidopropyl PG-dimmonium chloride phosphate (a stearyl derived phospholipid) also containing cetyl alcohol available from Mona Industries Inc. of Paterson, NJ.
[2]Behenylphospholipid is a behenyl derived phospholipid similar in composition to Phospholipid SV.

Samples A, B, E and F were uniform and stable but had low viscosity. Samples C, D, G, and H were opaque and pearlescent with higher viscosity values. CHG was added as a 20% solution in water to a final concentration of 0.5% by weight to formulations C, D, G, and H. The viscosity was measured one day after adding CHG. The results indicate that the thickener systems are tolerant to CHG addition and that addition of CHG may actually increase the viscosity for these systems. It should be noted that Phospholipid SV, like many single long chain quaternary amine-containing surfactants, is reported to have significant antimicrobial activity.

Example 31: Alkyl Betaine/Polyethoxylated Alkyl Alcohol Thickener System

The following formulations systems were prepared according to the procedure of Example 28. After measuring the viscosity, CHG was added as a 20% solution to a final concentration of 0.5% by weight. The viscosity was measured again one day later.

| Component | Formulation | | | |
|---|---|---|---|---|
| | A | B | C | D |
| | Amount (grams) | | | |
| Incronam B-40[1] (40% solution in water) | 2.70 | 2.03 | 1.35 | 0.68 |
| Nikkol BB-5 | 0.27 | 0.54 | 0.81 | 1.08 |
| Ethanol:water 60:40 | 42.03 | 42.44 | 42.82 | 43.25 |
| Viscosity (cps) | 40,700 | 52,600 | 52,500 | 35,300 |
| Viscosity (cps) post-CHG Addition | 52,000 | 54,500 | 54,000 | 38,000 |

[1]Incronam B-40 = behenyl betaine available from Croda Inc. of Parsippeny, NJ.

Formulation A and B were opaque with some elasticity. Formulations C and D were similar but were more elastic. All formulations were homogenous after adding CHG and the CHG actually increased the viscosity of the formulations.

Example 32: Hydroxyfunctional Ester Containing Thickener Systems

Behenyl Lactate was prepared by reacting methyl lactate (Aldrich Chemical Company, Inc. of Milwaukee, Wis.) with Lanette 22 (behenyl alcohol, 90%, Henkel Corp. of Ambler, Pa.) in a transesterification reaction according to the following method: 0.2 g sodium hydride (60% in mineral oil) was added to 32.6 grams Lanette 22 at 70° C. in a 3-neck 250 ml glass flask purged with nitrogen and inserted with overhead stirrer, Dean Stark trap, thermometer, and condenser. To this was slowly added 9.4 g of methyl lactate and the contents were slowly heated to 160° C. and held at that temperature for one hour. At this temperature over 2 ml of methanol was collected. The contents were heated to 200° C. with a nitrogen sweep to remove any volatile components. After approximately 15 minutes at 200° C. the contents were cooled. Upon cooling the product crystallized and had a melting point of approximately 57° C.

The following thickener systems were prepared including subsequent addition of CHG as described in Example 31.

| Component | Formulation | | | | | | | | | | | |
|---|---|---|---|---|---|---|---|---|---|---|---|---|
| | A | B | C | D | E | F | G | H | I | J | K | L |
| | Amount (grams) | | | | | | | | | | | |
| Behenyl lactate | 1.08 | 0.81 | 0.54 | 0.27 | 1.08 | 0.81 | 0.54 | 0.27 | 1.08 | 0.81 | 0.54 | 0.27 |
| Nikkol BB-5 | 0.27 | 0.54 | 0.81 | 1.08 | | | | | | | | |
| Lanette 22 | | | | | 0.27 | 0.54 | 0.81 | 1.08 | | | | |

-continued

| Component | Formulation | | | | | | | | | | | |
|---|---|---|---|---|---|---|---|---|---|---|---|---|
| | A | B | C | D | E | F | G | H | I | J | K | L |
| Incroquat DBM90 (90% in isopropyl alcohol) | | | | | 0.25 | 0.25 | 0.25 | 0.25 | 0.30 | 0.60 | 0.90 | 1.20 |
| Ethanol:water 60:40 | 43.65 | 43.65 | 43.65 | 43.65 | 43.40 | 43.40 | 43.40 | 43.40 | 43.62 | 43.59 | 43.56 | 43.53 |
| Viscosity (cps) | 3,300 | 122,000 | 90,700 | 96,000 | 164,000 | 206,000 | 205,000 | 306,000 | 190,000 | 255,000 | 306,000 | 128,000 |
| Viscosity (cps) post CHG addition | 875 | 92,500 | 76,300 | 71,500 | 188,000 | 193,000 | 207,000 | 214,000 | 207,000 | 256,000 | 266,000 | 233,000 |

The results show that behenyl lactate is a useful emulsifier for the purposes of the present invention. Behenyl lactate forms homogenous high viscosity emulsions in a variety of systems over a broad range of thickener ratios. Although sample A was low in viscosity, Samples B–D formed very pearlescent viscoelastic compositions. Samples E–L formed very viscous gel-like compositions. The compositions are also stable to CHG addition.

Example 33: Alkylene Monoglyceride/Ester/Amine Oxide thickener System

The following thickener systems were prepared by heating separately the solvent and the thickener system to 75° C. The solvent was added to the thickener system rapidly followed by homogenization on a Silverson L4R at maximum speed for 15 seconds followed by stirring with an overhead paddle stirrer in a glass container immersed in a 5–10° C. water bath. Each composition was mixed for 3 minutes after which the composition cooled sufficiently for the emulsifiers to solidify. The viscosity was measured as described above. To each sample was then added CHG as a 20% solution in water to a final concentration of 0.5% by weight. The CHG was mixed in well using a spatula and the sample was allowed to equilibrate for 24 hours. The viscosity was then measured again.

| | Composition | | | |
|---|---|---|---|---|
| Component | A | B | C | D |
| | Amount (grams) | | | |
| Glycerol monoeurucate[1] | 1.20 | 0.90 | 0.60 | 0.30 |
| Kemester 9022 | 0.27 | 0.54 | 0.81 | 1.08 |
| Incroquat DBM-90 | 0.25 | 0.25 | 0.25 | 0.25 |
| Ethanol:water 60:40 | 43:28 | 43:31 | 43:34 | 43:37 |
| Viscosity (cps) | 630 | 105,000 | 149,000 | 173,000 |
| Viscosity (cps) post CHG addition | 9,200 | 110,000 | 205,000 | 202,000 |

[1]sample obtained from Croda Inc. of Parsippeny, New Jersey and consisted of 90% monoeurucate, 8% dieurucate and 2% trierucate by weight.

Composition A was bluish translucent but had a low viscosity. Composition B was similar to A but much more viscous than Composition A. Composition C was semi-opaque and even more viscous than Composition B. Sample D was opaque white with a fairly high viscosity.

Example 34: Viscosity as a Function of Shear Rate

The following example illustrates the pseudoplastic rheology and shear sensitivity of the compositions of the present invention. The viscosity was measured as a function of shear rate using a Rheometrics Dyanamic Analyzer (RDA-II) with a 25 mm cone/plate fixture with a cone angle of 0.1 rad at a temperature of 25° C. Entrapped air was removed from the samples prior to testing by centrifugation. The viscosity was measured in steady shear by keeping the rate of rotation constant. This was done over a shear rate range of 0.06–40 per second. The samples used for this testing were prepared according to Example 1, Sample A (Brij 78) and Example 32, Sample B. The following results were obtained:

| | Viscosity (cps) | |
|---|---|---|
| Shear Rate | Ex. 1, Sample A | Ex. 32, Sample B |
| Brookfield LVDV-I+ | 294000 | 92500 |
| 0.06 Rheometrics | 42000 | 7200 |
| 0.10 Rheometrics | 37000 | 5700 |
| 1.0 Rheometrics | 14000 | 2300 |
| 3.0 Rheometrics | 3800 | 680 |
| 10.0 Rheometrics | 2100 | 420 |
| 40.0 Rheometrics | 720 | 140 |

The results indicate that the viscosity is very shear sensitive. This allows the compositions to dispense well into the hand without running and yet allows the compositions to spread easily across the skin surface.

Example 35: Foam Formulation 90 g of the formulation of Example 25 was charged to a glass pressure vessel at room temperature. To this was added 7 g propane and 3 g isobutane. The addition of the propellant resulted in a dramatic drop in viscosity. The viscosity appeared to be about the viscosity of water. The formulation appeared as a single emulsified opaque white liquid. After sitting for several days the propellant formed a separate phase but was easily reemulsified by shaking. The formulation produced a white foam.

Example 36

This example demonstrates that monovalent salts of acids are useful as co-emulsifiers in the present invention.

The samples were prepared according to the formulae outlined in the table below by placing all components in a 4-oz. jar. The jar was capped and heated to 65° C. until all components were dissolved. The jar was then swirled to mix the components, removed from the heat and allowed to cool to ambient temperature. Viscosity measurements were taken as identified in the table. Separation tests were done as outlined in Example 3.

| | Sample | |
|---|---|---|
| | A | B |
| Component | Amount (grams) | |
| BB-5 | 0.96 | 0.96 |
| Sodium Stearate | 0.36 | 0.96 |

-continued

| | Sample | |
|---|---|---|
| | A | B |
| Component | Amount (grams) | |
| 190 Ethanol | 42.00 | 41.60 |
| Deionized Water | 16.70 | 16.50 |
| Viscosity (cps) | 5,904[1] | 320,000[2] |
| % Separation (by Volume) | 0 | 0 |

[1]Measurements taken at ambient temperature using a Brookfield LVDV-I+ viscometer with a TC Heliopath Spindle at 0.3 rpm.
[2]Measurements taken at ambient temperature using a Brookfield LVDV-I+ viscometer with a TD Heliopath Spindle at 0.3 rpm.

Example 37: Alkyl Alcohol/Long Chain Polyethoxylate/Quaternary Amine Thickener System The following formulation was prepared using the compounds listed below in the percentages indicated.

| Ingredient Number | Ingredient | wt. Percent |
|---|---|---|
| Part A | | |
| 1 | Beheneth Ether (BB-10)[1] | 1.08 |
| 2 | Dibehenyldimethylammonium methosulfate[2] | 0.25 |
| 3 | Behenyl Alcohol[3] (BE-22) | 0.67 |
| Part B | | |
| 4 | Diisopropyl Dimerate[4] | 1.50 |
| 5 | Squalane[5] | 1.50 |
| 6 | Dimethicone L45/350[6] | 0.50 |
| Part C | | |
| 7 | Polyethylene Glycol 900[7] | 1.26 |
| 8 | Polyethylene Glycol 600[8] | 0.54 |
| 9 | Glycerol[9] | 0.72 |
| 10 | Water | 25.11 |
| 11 | Ethyl Alcohol | 61.86 |
| 12 | Chlorhexidine[10] Gluconate solution | 5.00 |

[1]Beheneth-10 available from Barnet Products Corporation, Englewood Cliffs, NJ
[2]Dibehenyldimethylammonium methosulfate as Incroquat DBM-90 from Croda, Inc, Parsippany, NY
[3]Behenyl alcohol as Cachelot BE-22 available from M. Michel & Company, Inc, New York, NY
[4]Diisopropylpalmitate as Pripure from Unichema North America, Chicago, Ill.
[5]Squalane from Barnet Products Corporation, Englewood Cliffs, NJ
[6]Diemthicone L45/350 from OSI Spoecialties, Inc. Danbury, CT
[7]Polyethylene glycol 900 from Dow Chemical, Midland, MI
[8]Polyethylene glycol 600 as Carbowax 600 from Union Carbide
[9]Glycerol as Optim from Dow Chemical, Midland, MI
[10]Chlorhexidine, Medichem, Barcelona, Spain 20.1% wt/vol. in water Ethanol used was 200 proof A total batch size of 500 g of the composition was prepared by placing the ingredients of Parts A and B into a sealed one quart glass jar followed by heating to 90° C. until all components were melted (about 75 min.). The ingredients of Part C along with the water were placed into a one 200 ml glass jar and heated to 90° C. (also bout 75 min.) Part C was added to the Part A/B molten mixture and homogenized using the Silverson homogenizer at full speed for 60 seconds. This was sealed and heated at 56° C. for approximately 1 hour and then allowed to cool on a roller. Once cooled the ethanol was added followed by sealing and shaking the contents vigorously for 60 seconds until the sample was homogenous. The contents were once again sheared on the homogenizer at full speed for 60 seconds followed by vigorous shaking for 20 seconds and repeat homogenization for 60 seconds.

This formula was applied by numerous volunteers and found to have very nice cosmetic properties.

While in accordance with the patent statutes, description of the preferred weight fractions, processing conditions, and product usages have been provided, the scope of the invention is not intended to be limited thereto or thereby. Various modifications and alterations of the present invention will be apparent to those skilled in the art without departing from the scope and spirit of the present invention. The Examples described in this application are illustrative of the possibilities of varying the type, quantity and ratio of composition as well as the methods for making formulations of the present invention. The complete disclosures of all patents, patent applications, and publications recited herein are incorporated by reference, as if individually incorporated by reference.

What is claimed is:

1. A hydroalcoholic composition comprising:
   a) a lower alcohol and water in a weight ratio of about 35:65 to about 95.5; and
   b) a thickener system present in an amount of about 0.5% by weight to about 8% by weight, based on the total weight of the composition; wherein the thickener system comprises at least two solid emulsifiers, each in an amount of at least about 0.05% by weight, based on the total weight of the composition; wherein at least one emulsifier comprises:
      (i) at least one hydrophobic group selected from the group consisting of:
         (A) an alkyl group of at least 16 carbon atoms;
         (B) an alkenyl group of at least 16 carbon atoms; and
         (C) an aralkyl or an aralkenyl group of at least 20 carbon atoms; and
      (ii) at least one hydrophilic group selected from the group consisting of:
         (A) an amide group;
         (B) a short chain ester of a long chain alcohol or acid;
         (C) a polyglucoside group having 1–10 glucose units;
         (D) a polyglycerol ester group having 1–15 glycerol units;
         (E) a secondary amine group;
         (F) a tertiary amine group;
         (G) a quaternary amine group;
         (H) an anionic group;
         (I) a zwitterionic group; and
         (J) combinations of these groups;
   wherein the composition has a viscosity of at least about 4,000 centipoise at 23° C. in the absence of polymeric thickeners.

2. The composition of claim 1 wherein the thickener system further comprises at least one emulsifier having:
   (i) at least one hydrophobic group selected from the group consisting of:
      (A) an alkyl group of at least 16 carbon atoms;
      (B) an alkenyl group of at least 16 carbon atoms; and
      (C) an aralkyl or an aralkenyl group of at least 20 carbon atoms; and
   (ii) at least one hydrophilic group selected from the group of:
      (A) an ethylene oxide- and/or propylene oxide-containing group, which is bonded to the hydrophobic group through an ether or ester bond and optionally terminated with a (C1–C36)alkyl ester, (C2–C36)alkenyl ester, or (C6–C36)alkaryl ester;
      (B) an alcohol group;

(C) a polyhydric alcohol group;
(D) an ester or ether group of a polyhydric alcohol or polyalkoxylated derivative thereof;
(E) an ester or ether group of sorbitan or polyalkoxylated derivative thereof; and
(F) combinations of these groups.

3. The composition of claim 1 which does not separate by more than about 10% by volume when centrifuged for 30 minutes at 2275× g.

4. The composition of claim 1 wherein the hydrophobic and hydrophilic groups are selected to provide a thickener system having a weight average hydrophile/lipophile balance of about 8 to about 12.

5. The composition of claim 1 further comprising at least one emollient distinct from the thickener system.

6. The composition of claim 5 wherein the at least one emollient is in the form of a wax or a liquid.

7. The composition of claim 6 wherein both wax and liquid emollients are present and the ratio of wax to liquid emollients is from about 1:5 to about 5:1.

8. The composition of claim 6 wherein the at least one emulsifier is in the form of a wax or a liquid.

9. The composition of claim 8 wherein the ratio of wax emollients and wax emulsifiers to liquid emollients and liquid emulsifiers is from about 1:5 to about 5:1.

10. The composition of claim 6 wherein the emollient is a dialkoxy dimethicone or a polyether/polysiloxane copolymer.

11. The composition of claim 1 further comprising an antimicrobial agent distinct from the lower alcohol.

12. The composition of claim 11 wherein the antimicrobial agent is selected from the group consisting of a chlorhexidine salt, iodine, a complexed form of iodine, parachlorometaxylenol, triclosan, hexachlorophene, Lauricidin, a phenol, a surfactant having a long chain hydrophobic group and a quaternary group, a quaternary silane, hydrogen peroxide, silver, a silver salt, silver oxide, silver sulfadiazine, and mixtures thereof.

13. The composition of claim 12 wherein the antimicrobial agent is selected from the group consisting of a chlorhexidine salt, iodine, a complexed form of iodine, parachlorometaxylenol, triclosan, and mixtures thereof.

14. The composition of claim 13 wherein the antimicrobial agent is chlorhexidine digluconate.

15. The composition of claim 1 further comprising a salt.

16. The composition of claim 1 wherein the lower alcohol is a C1–C4 alcohol.

17. The composition of claim 16 wherein the lower alcohol is selected from the group consisting of ethanol, 2-propanol, n-propanol, and mixtures thereof.

18. The composition of claim 17 wherein the lower alcohol is ethanol.

19. The composition of claim 1 wherein the thickener system is present in an amount of about about 0.75% by weight to about 5% by weight, based on the total weight of the composition.

20. The composition of claim 19 wherein the thickener system is present in an amount of about 1.0% by weight to about 3.5% by weight, based on the total weight of the composition.

21. The composition of claim 1 further comprising a stabilizer.

22. The composition of claim 21 wherein the stabilizer is selected from the group consisting of alkyl pendant polymers and borate ion.

23. The composition of claim 1 further comprising polydimethylsiloxane or derivatives thereof selected from the group consisting of polyether polysiloxane copolymers, polyalkyl siloxanes, polyaryl/alkyl/siloxanes, polysiloxane polyalkylene copolymers, and dialkoxy dimethyl siloxanes.

24. The composition of claim 1 further comprising a therapeutic agent.

25. The composition of claim 1 wherein the emulsifier includes at least two hydrophobic groups.

26. The composition of claim 25 wherein the emulsifier is a quaternary ammonium salt.

27. The composition of claim 1 wherein at least one emulsifier is selected from the group consisting of an alkyl polyglucoside, an alkenyl polyglucoside, a short chain ester of a long chain alcohol, a short chain ester of a long chain acid, a polyglycerol ester, a quaternary amine, a tertiary amine and protonated salts thereof, an amine oxide, a zwitterionic compound, an alkyl amide, an alkenyl amide, an anionic compound, and mixtures thereof.

28. The composition of claim 2 wherein the ethylene oxide- and/or propylene oxide-containing group is a polyethylene glycol group or a polypropylene glycol group.

29. The composition of claim 2 wherein at least one emulsifier is selected from the group consisting of a poly(ethoxylated and/or propoxylated)alcohol, a poly(ethoxylated and/or propoxylated)ester, an alkyl, alkenyl, aralkyl or aralkenyl derivative of a poly(ethoxylated and/or propoxylated)alcohol an alkyl, alkenyl, aralkyl or aralkenyl, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof.

30. The composition of claim 1 wherein the thickener system comprises a short chain ester of a long chain alcohol or acid, an alkyl or alkenyl alcohol, and a quaternary amine.

31. The composition of claim 1 wherein the thickener system comprises an alkyl polyglucoside, a polyethoxylated alcohol, and a quaternary amine.

32. The composition of claim 1 wherein the thickener system comprises an alkyl polyglucoside, a polyethoxylated alcohol, and an amine oxide.

33. The composition of claim 1 wherein the thickener system comprises an alkyl polyglucoside and a tertiary amine.

34. The composition of claim 1 wherein the thickener system comprises an alkyl polyglucoside and a quaternary amine.

35. The composition of claim 1 wherein the thickener system comprises a polyglycerol ester, a polyethoxylated alcohol, and an alkyl or alkenyl alcohol.

36. The composition of claim 1 wherein the thickener system comprises a polyglycerol ester, a polyethoxylated alcohol, an alkyl or alkenyl alcohol, and a short chain ester of a long chain alcohol or acid.

37. The composition of claim 1 wherein the thickener system comprises a polyglycerol ester, a polyethoxylated alcohol, and a quaternary amine.

38. The composition of claim 1 wherein the thickener system comprises a polyglycerol ester, a short chain ester of a long chain alcohol or acid, and a quaternary amine.

39. The composition of claim 1 wherein the thickener system comprises a polyglycerol ester, an amine oxide, and a quaternary amine.

40. The composition of claim 1 wherein the thickener system comprises an alkyl or alkenyl alcohol, a short chain ester of a long chain alcohol or acid, and a quaternary amine.

41. The composition of claim 1 wherein the thickener system comprises an alkyl or alkenyl alcohol, a short chain ester of a long chain alcohol or acid, and an amine oxide.

42. The composition of claim 1 wherein the thickener system comprises a short chain ester of a long chain alcohol or acid, a polyethoxylated alcohol, and a quaternary amine.

43. The composition of claim 1 wherein the thickener system comprises a short chain ester of a long chain alcohol or acid, and a quaternary amine.

44. The composition of claim 1 wherein the thickener system comprises an alkyl betaine and a polyethoxylated alcohol.

45. The composition of claim 1 wherein the thickener system comprises an alkyl phospholipid and a polyethoxylated alcohol.

46. The composition of claim 1 wherein the composition comprises a short chain ester of a long chain alcohol or acid, an alkyl alcohol, and dialkoxydimethicone.

47. The composition of claim 1 wherein the thickener system comprises a short chain ester of a long chain alcohol or acid and a polyethoxylated alcohol.

48. The composition of claim 1 wherein the thickener system comprises a short chain ester of a long chain alcohol or acid and a quaternary amine.

49. The composition of claim 1 wherein the sickener system comprises a polyglycerol ester and a polyethoxylated alcohol.

50. The composition of claim 1 wherein the thickener system comprises an alkyl carboxylate and a polyethoxylated alcohol.

51. The composition of claim 1 wherein the thickener system comprises a short chain ester of a long chain alcohol, an alkyl alcohol, and a quaternary amine.

52. The composition of claim 1 wherein the thickener system comprises a quaternary amine, an alkyl alcohol, and a polyethoxylated alcohol.

53. The composition of claim 1 wherein the lower alcohol and water are present in a weight ratio of about 60:40 to about 75:25.

54. The composition of claim 1 wherein the thickener system comprises one or more emulsifiers capable of forming an alcoholic composition having a viscosity of at least about 10,000 centipoise at 23° C. in the absence of a polymeric thickener.

55. The composition of claim 1 which has a viscosity of about 80,000 centipoise to about 500,000 centipoise at 23 ° C.

56. The composition of claim 1 which is in the form of a lotion.

57. The composition of claim 1 which is in the form of a foam.

58. The composition of claim 1 wherein the amide group has the structure —NHC(O)R''' or —C(O)NHR''', wherein R'' is hydrogen or an alkyl group of 1–10 carbon atoms optionally substituted with N, O, or S atoms.

59. The composition of claim 1 wherein the anionic group is selected from the group consisting of a sulfate, a sulfonate, a phosphate, a phosphonate, and a carboxylate group.

60. The composition of claim 1 wherein the zwitterionic group has the formula:

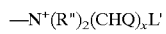

or

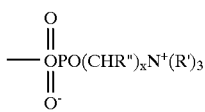

wherein:

each R'' is independently hydrogen, an alkyl group, an alkenyl group, an alkyl carboxyl group, or an alkenyl carboxyl group, which alkyl or alkenyl groups are optionally substituted with N, O, or S atoms;

Q is hydrogen or hydroxyl;

x is 1 to 4; and

L' is —$CO_2^-$, —$OP(O)(O^-)(O^-M^-)$, —$(O)P(OR''')(O)(O^-M^+)$, —$SO_2O^-$, or —$OSO_2O^-$ wherein:

R''' is hydrogen or an alkyl group of 1–10 carbon atoms optionally substituted with N, O, or S atoms;

$M^+$ is a positively charged counterion present in a molar ratio necessary to achieve a net neutral charge on the emulsifier and is selected from the group consisting of hydrogen, sodium, potassium, lithium, ammonium, calcium, magnesium, and $N^+R'_4$.

61. The composition of claim 1 further comprising an antifungal agent.

62. A method of dispensing the composition of claim 1 comprising dispensing the composition in a discrete and substantially uniform amount.

63. A hydroalcoholic composition comprising:
  a) a lower alcohol and water in a weight ratio of about 35:65 to about 95:5;
  b) a thickener system present in an amount of about 0.5% by weight to about 8% by weight, based on the total weight of the composition; wherein the thickener system comprises at least two emulsifiers, each in an amount of at least about 0.05% by weight, based on the total weight of the composition;

wherein at least one emulsifier comprises:
  (i) at least one hydrophobic group selected from the group consisting of:
    (A) an alkyl group of at least 16 carbon atoms;
    (B) an alkenyl group of at least 16 carbon atoms; and
    (C) an aralkyl or an aralkenyl group consisting of at least 20 carbon atoms; and
  (ii) at least one hydrophilic group selected from the group of:
    (A) an amide group;
    (B) a short chain ester of a long chain alcohol or acid;
    (C) a polyglucoside group having 1–10 glucose units;
    (D) a polyglycerol ester group having 1–15 glycerol units;
    (E) a secondary amine group;
    (F) a tertiary amine group;
    (G) a quaternary amine group;
    (H) an anionic group;
    (I) a zwitterionic group; and
    (J) combinations of these groups; and wherein at least one emulsifier comprises:
  (i) at least one hydrophobic group selected from the group of:
    (A) an alkyl group of at least 16 carbon atoms;
    (B) an alkenyl group of at least 16 carbon atoms; and
    (C) an aralkyl or an aralkenyl group consisting of at least 20 carbon atoms; and (ii) at least one hydrophilic group selected from the group of:
  (A) an ethylene oxide- and/or propylene oxide-containing group, which is bonded to the hydrophobic group through an ether or ester bond and optionally terminated with a (C1–C36)alkyl ester, (C2–C36)alkenyl ester, or (C6–C36)alkaryl ester;
  (B) an alcohol group;
  (C) a polyhydric alcohol group;
  (D) an ester or ether group consisting of a polyhydric alcohol or polyalkoxylated derivative thereof;
  (E) an ester or ether group of sorbitan or polyalkoxylated derivative thereof; and
  (F) combinations of these groups; and
c) an antimicrobial agent distinct from the lower alcohol;
wherein the composition has a melt temperature of greater than about 35° C. and the at least two emulsifiers provide the composition with a viscosity of at least about 4,000 centipoise at 23° C.

64. The composition of claim 63 which has a melt temperature of greater than about 40° C.

65. The composition of claim 63 further comprising an antifungal agent.

66. A method of dispensing the composition of claim 63 comprising dispensing the composition in a discrete and substantially uniform amount.

67. A method of preparing a stable hydroalcoholic composition, the method comprising:
a) preparing a thickener system comprising at least two emulsifiers, each in an amount of at least about 0.05% by weight, based on the total weight of the composition; wherein at least one emulsifier comprises:
  (i) at least one hydrophobic group selected from the group consisting of:
    (A) an alkyl group of at least 16 carbon atoms;
    (B) an alkenyl group of at least 16 carbon atoms; and
    (C) an aralkyl or an aralkenyl group of at least 20 carbon atoms; and
  (ii) at least one hydrophilic group selected from the group consisting of:
    (A) an amide group;
    (B) a short chain ester of a long chain alcohol or acid;
    (C) a polyglucoside group having 1–10 glucose units;
    (D) a polyglycerol ester group having 1–15 glycerol units;
    (E) a secondary amine group;
    (F) a tertiary amine group;
    (G) a quaternary amine group;
    (H) an anionic group;
    (I) a zwitterionic group; and
    (J) combinations of these groups; and
b) combining the thickener system with a solvent system at a temperature sufficient to melt the thickener system and form a composition having a viscosity of at least about 4,000 centipoise at 23° C. in the absence of polymeric thickeners; wherein the solvent system comprises a lower alcohol and water in a weight ratio of about 35:65 to about 95:5.

68. The method of claim 67 wherein the composition has a melt temperature of greater than about 40° C.

69. The method of claim 67 wherein the thickener system further comprises at least one emulsifier having:
(i) at least one hydrophobic group selected from the group consisting of:
  (A) an alkyl group of at least 24 carbon atoms;
  (B) an alkenyl group of at least 24 carbon atoms; and
  (C) an aralkyl or an aralkenyl group of at least 24 carbon atoms; and
(ii) at least one hydrophilic group selected from the group of:
  (A) an ethylene oxide- and/or propylene oxide-containing group, which is bonded to the hydrophobic group through an ether or ester bond and optionally terminated with a (C1–C36)alkyl ester, (C2–C36)alkenyl ester, or (C6–C36)alkaryl ester;
  (B) an alcohol group;
  (C) a polyhydric alcohol group;
  (D) an ester or ether group of a polyhydric alcohol or polyalkoxylated derivative thereof;
  (E) an ester or ether group of sorbitan or polyalkoxylated derivative thereof; and
  (F) combinations of these groups.

70. The method of claim 67 further comprising cooling the composition to less than about 30° C.

71. The method of claim 70 further comprising adding an antimicrobial to said cooled composition.

72. The method of claim 67 further comprising high shear mixing the composition while above its melt temperature.

73. The method of claim 67 wherein the composition further comprises an antifungal agent.

74. A method of preparing a stable hydroalcoholic composition, the method comprising:
a) heating a thickener system to a temperature sufficient to melt it; the thickener system comprising at least two emulsifiers, each in an amount of at least about 0.05% by weight, based on the total weight of the composition; wherein at least one emulsifier comprises:
  (i) at least one hydrophobic group selected from the group consisting of:
    (A) an alkyl group of at least 16 carbon atoms;
    (B) an alkenyl group of at least 16 carbon atoms; and
    (C) an aralkyl or an aralkenyl group of at least 20 carbon atoms; and
  (ii) at least one hydrophilic group selected from the group consisting of:
    (A) an amide group;
    (B) a short chain ester of a long chain alcohol or acid;
    (C) a polyglucoside group having 1–10 glucose units;
    (D) a polyglycerol ester group having 1–15 glycerol units;
    (E) a secondary amine group;
    (F) a tertiary amine group;
    (G) a quaternary amine group;
    (H) an anionic group;
    (I) a zwitterionic group; and
    (J) combinations of these groups; and
b) heating water to a temperature above the melt temperature of the thickener system;
c) combining the thickener system and the water; and
d) adding a lower alcohol to the thickener system and water to form a composition having a viscosity of at least about 4,000 centipoise at 23° C. in the absence of polymeric thickeners; wherein the lower alcohol and water are present in a weight ratio of about 35:65 to about 95:5.

75. The method of claim 74 wherein the thickener system further comprises at least one emulsifier having:
(i) at least one hydrophobic group selected from the group consisting of:
  (A) an alkyl group of at least 16 carbon atoms;

(B) an alkenyl group of at least 16 carbon atoms; and
(C) an aralkyl or an aralkenyl group of at least 20 carbon atoms; and
(ii) at least one hydrophilic group selected from the group consisting of:
(A) an ethylene oxide- and/or propylene oxide-containing group, which is bonded to the hydrophobic group through an ether or ester bond and optionally terminated with a (C1–C36)alkyl ester, (C2–C36)alkenyl ester, or (C6–C36)alkaryl ester;
(B) an alcohol group;
(C) a polyhydric alcohol group;
(D) an ester or ether group of a polyhydric alcohol or polyalkoxylated derivative thereof;
(E) an ester or ether group of sorbitan or polyalkoxylated derivative thereof; and
(F) combinations of these groups.

76. The method of claim 75 wherein the ethylene oxide- and/or propylene oxide-containing group is a polyethylene glycol group or a polypropylene glycol group.

77. The method of claim 75 further comprising cooling the thickener system and water combination before adding the lower alcohol.

78. A hydroalcoholic composition produced from the method of claim 67.

79. A hydroalcoholic composition produced from the method of claim 74.

80. The method of claim 74 wherein the composition further comprises an antifingal agent.

* * * * *

UNITED STATES PATENT AND TRADEMARK OFFICE
CERTIFICATE OF CORRECTION

PATENT NO.     : 5,951,993
DATED          : September 14, 1999
INVENTOR(S)    : Scholz et al.

It is certified that error appears in the above-identified patent and that said Letters Patent is hereby corrected as shown below:

Title page,
Item [56], References Cited, OTHER PUBLICATIONS, "G.M. Eccleston" 2nd reference, delete "alcoholics" and insert -- alcohols -- therefor.

Column 50,
Line 20, delete "95.5" and insert -- 95:5 -- therefor.
Line 49, delete "polymeric" and insert -- auxiliary -- therefor.
Line 60, insert -- consisting -- after the phrase "selected from the group".

Column 52,
Line 22, delete the "a" after the phrase "from the group consisting of" and insert -- an alkyl, alkenyl, aralkyl or aralkenyl -- therefor.
Line 26, delete "an alkyl, alkenyl, aralkyl or aralkenyl".

Column 53,
Line 26, delete "sickener" and insert -- thickener -- therefor.
Line 46, delete 'polymeric" and insert -- auxiliary -- therefor.
Line 49, insert -- in the absence of an auxiliary thickener." after "23°C."
Line 57, delete "R''''" occurring before the phrase "is a hydrogen or an alkyl group" and insert -- R''' -- therefor.

Column 54,
Line 16, delete "(O$^-$ M$^-$)" that occurs after "—OP(O)(O$^-$)" and insert -- (O$^-$ M$^+$) -- therefor.
Line 24, delete "N$^+$R'$_4$" and insert -- N$^+$R''$_4$ -- therefor.
Line 48, insert -- consisting -- after the phrase "selected from the group".
Line 63, insert -- consisting -- after the phrase "selected from the group".

Column 55,
Line 2, insert -- consisting -- after the phrase "selected from the group".
Line 10, delete "consisting" occurring after the phrase "an ester or ether group".
Line 19, insert -- in the absence of an auxiliary thickener -- after the phrase "4,000 centipoise at 23 C".
Line 57, delete "polymeric" and insert -- auxiliary -- therefor.

UNITED STATES PATENT AND TRADEMARK OFFICE
CERTIFICATE OF CORRECTION

PATENT NO. : 5,951,993
DATED : September 14, 1999
INVENTOR(S) : Scholz et al.

It is certified that error appears in the above-identified patent and that said Letters Patent is hereby corrected as shown below:

Column 56,
Line 4, insert -- consisting -- after the phrase "selected from the group".
Line 59, delete "polymeric" and insert -- auxiliary -- therefor.

Signed and Sealed this

Twenty-eighth Day of December, 2004

JON W. DUDAS
*Director of the United States Patent and Trademark Office*